US012036355B2

(12) United States Patent
Dunne et al.

(10) Patent No.: US 12,036,355 B2
(45) Date of Patent: Jul. 16, 2024

(54) NEBULIZER AND CONTAINER

(71) Applicant: Boehringer Ingelheim International GmbH, Ingelheim am Rhein (DE)

(72) Inventors: Stephen Terence Dunne, Oporto (PT); Dana Huesch, Bad Soden (DE); Peter Rolf Werner Langguth, Biebergemünd (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 889 days.

(21) Appl. No.: 17/051,382

(22) PCT Filed: May 3, 2019

(86) PCT No.: PCT/EP2019/061343

§ 371 (c)(1),
(2) Date: Oct. 28, 2020

(87) PCT Pub. No.: WO2019/211424

PCT Pub. Date: Nov. 7, 2019

(65) Prior Publication Data

US 2021/0228822 A1 Jul. 29, 2021

(30) Foreign Application Priority Data

May 4, 2018 (EP) .................................... 18170839
Jun. 15, 2018 (EP) .................................... 18177939

(51) Int. Cl.
*A61M 11/00* (2006.01)
*A61F 9/00* (2006.01)
(Continued)

(52) U.S. Cl.
CPC ......... *A61M 11/007* (2014.02); *A61F 9/0008* (2013.01); *A61K 9/0078* (2013.01);
(Continued)

(58) Field of Classification Search
CPC .. A61M 11/00; A61M 11/001; A61M 11/002; A61M 11/003; A61M 11/006;
(Continued)

(56) References Cited

U.S. PATENT DOCUMENTS 5,152,435 A 10/1992 Stand
5,539,021 A * 7/1996 Pate .......................... C08J 3/09
516/929

(Continued)

FOREIGN PATENT DOCUMENTS

EP 1820493 A2 8/2007
EP 2614848 A1 7/2013

(Continued)

OTHER PUBLICATIONS

Machine translation of WO-2009047173-A2.*

(Continued)

*Primary Examiner* — Joseph D. Boecker
(74) *Attorney, Agent, or Firm* — Matthew B. Dernier, Esq.

(57) ABSTRACT

A system includes a nebulizer for nebulizing a fluid from a container and such a container containing a fluid and are proposed. The fluid is a non-newtonian fluid, in form of a suspension or emulsion or a liposomal fluid or a gel. The nebulizer includes a fluid pump for withdrawing the fluid in doses from the container and pressurizing the respective doses for nebulization through nozzle channels having a hydraulic diameter in the range of 3 to 20 microns at an operational pressure of 5 to 250 MPa.

32 Claims, 15 Drawing Sheets

(51) Int. Cl.

| | |
|---|---|
| ***A61K 9/00*** | (2006.01) |
| ***A61K 9/107*** | (2006.01) |
| ***A61K 9/127*** | (2006.01) |
| ***A61K 31/58*** | (2006.01) |
| ***A61K 47/24*** | (2006.01) |
| ***A61K 47/28*** | (2006.01) |
| ***A61M 15/00*** | (2006.01) |
| ***B05B 9/08*** | (2006.01) |
| ***B05B 11/00*** | (2023.01) |
| ***B05B 11/02*** | (2023.01) |
| ***B05B 11/10*** | (2023.01) |
| ***B05B 17/00*** | (2006.01) |

(52) U.S. Cl.
CPC .............. *A61K 9/127* (2013.01); *A61K 47/24* (2013.01); *A61K 47/28* (2013.01); *B05B 9/0822* (2013.01); *B05B 17/00* (2013.01); *A61K 9/0048* (2013.01); *A61K 9/1075* (2013.01); *A61K 31/58* (2013.01); *A61M 15/0035* (2014.02); *A61M 2205/071* (2013.01); *B05B 11/0054* (2013.01); *B05B 11/026* (2023.01); *B05B 11/028* (2023.01); *B05B 11/1091* (2023.01)

(58) Field of Classification Search
CPC .. A61M 11/007; A61M 11/008; A61M 15/00; A61M 15/02; A61M 15/025; A61F 9/0008; A61K 9/0078; A61K 9/1075; A61K 9/127; A61K 47/24; A61K 47/28; B05B 17/00
See application file for complete search history.

(56) References Cited

U.S. PATENT DOCUMENTS 5,833,088 A 11/1998 Kladders
6,481,435 B2 11/2002 Hochrainer
6,988,496 B1 1/2006 Eicher
7,213,593 B2 5/2007 Hochrainer
7,314,187 B2 1/2008 Zierenberg
7,819,342 B2 10/2010 Spallek
9,283,333 B2 3/2016 Hausmann
10,973,763 B2 4/2021 Narain
11,207,474 B2 12/2021 Dunne
2001/0009151 A1* 7/2001 Hochrainer ............... B05B 7/24 128/200.14
2001/0032643 A1 10/2001 Hochrainer
2003/0064032 A1* 4/2003 Lamche ................. A61K 38/17 514/6.9
2003/0078551 A1* 4/2003 Hochrainer .......... A61M 11/006 604/295
2004/0010239 A1 1/2004 Hochrainer
2005/0263618 A1 12/2005 Spallek
2006/0016449 A1 1/2006 Eicher
2009/0192443 A1* 7/2009 Collins, Jr. ......... A61M 15/008 239/338
2011/0005517 A1 1/2011 Boeck
2012/0067343 A1* 3/2012 Wu ........................ A61K 47/26 128/200.23
2012/0321698 A1* 12/2012 Narain ............... G01N 15/0205 977/773
2013/0199521 A1* 8/2013 Hausmann ........... A61M 11/007 128/200.23
2013/0330400 A1* 12/2013 Perkins ................ A61K 9/1271 514/36
2016/0331863 A1 11/2016 Cawthon
2017/0203056 A1 7/2017 Dunne
2017/0224718 A1 8/2017 Levine
2017/0333922 A1 11/2017 Selby
2017/0360815 A1 12/2017 Latefi
2022/0168143 A1* 6/2022 Zhang .................. A61M 11/006

FOREIGN PATENT DOCUMENTS

JP 2014520124 A 8/2014
JP 2017521195 A 8/2017
WO 9114468 A1 10/1991
WO 9407607 A1 4/1994
WO 9606011 A2 2/1996
WO 9712687 A1 4/1997
WO 9736574 A1 10/1997
WO 9739831 A1 10/1997
WO 1998012511 A1 3/1998
WO 99007340 A1 2/1999
WO 9916530 A1 4/1999
WO 0023037 A1 4/2000
WO 0049988 A2 8/2000
WO 2003002045 A1 1/2003
WO 2004024340 A1 3/2004
WO 2005000476 A1 1/2005
WO 2005107837 A1 11/2005
WO 07101557 A2 9/2007
WO 2008138936 A2 11/2008
WO 2009047173 A2 4/2009
WO WO-2009047173 A2 * 4/2009 ........... A61K 9/0078
WO 2009115200 A1 9/2009
WO 2010094305 A1 8/2010
WO 2012007315 A1 1/2012
WO 2012162305 A1 11/2012
WO 2015060935 A1 4/2015
WO 2016012102 A1 1/2016
WO WO-2016012102 A1 * 1/2016 .......... A61M 11/007
WO 2016038357 A1 3/2016
WO 2016075433 A1 5/2016
WO WO-2017060386 A1 * 4/2017 .......... A61M 11/006
WO 2017129477 A1 8/2017

OTHER PUBLICATIONS

Machine translation of WO-2017060386-A1.*
International Search Report and Written Opinion for corresponding application PCT/EP2019/061343, 21 pages dated Jul. 10, 2019.
J. Junghanns and R. Müller, "Nanocrystal technology, drug delivery and clinical applications" International Journal of Nanomedicine, p. 295-309, Jan. 1, 2008.
C. Jabobs and R. Müller, "Production and Characterization of a Budesonide Nanosuspension for Pulmonary Adminsitration," Pharmaceutical Research, vol. 19, No. 2, p. 189-194, Feb. 1, 2002.

* cited by examiner

NEBULIZER AND CONTAINER

BACKGROUND

The present invention relates to a system comprising a nebulizer and a container according to the embodiments herein.

Nebulizers are used in various therapeutic areas, for instance for spraying fluids on the skin or into the eye or in form of inhalers for generating inhalable aerosols. Besides nebulizers comprising a propellant for the generation of the spray (for instances so called MDIs in case of inhalers), there are mechanical nebulizers for generating sprays. Mechanical nebulizers for spraying onto the skin typically comprise a so called finger pump attached to a container containing the fluid.

U.S. Pat. No. 5,152,435 discloses a finger pump system for delivering a quantity of ophthalmic solution onto the surface of the eye. The dispensing pump basically comprises a push button actuator having a nozzle member disposed therein, a cap member for receiving the push button and having a control ring for selectively limiting the downward travel of the actuator, and a pump chamber engaged in the cap member and in communication with the push button actuator for pressurizing a metered quantity of the ophthalmic solution (0.05 ml in the given example). The fluid stream is delivered with an impact pressure of 2.75-6.80 mmHg, thereby ensuring that it makes gentle contact with the surface of the eye. In regard to ophthalmic applications, the drawbacks of finger pumps are that they rely on the user to fully press for a full dose and for getting the designed size and velocity of the ejected droplets. Also the spray nozzle moves downwards when pressed so it is more difficult to direct the spray during its' generation.

WO 1998/012511 A2 discloses a device for applying fluid to the surface of the eye of a patient wherein the fluid (especially a liquid for cleaning or soothing the eye) is expelled from an orifice (which is stationary in the nebulizer housing/fixed during spray generation) as a mist. The device comprises a storage chamber being fluidically connected via a first valve to a charge chamber and a piston wherein the priming of the piston against a biasing means (spring) causes a dose of the fluid to enter the charge chamber. When dispensing the dose, the biasing means move the piston out of the priming position and causes the fluid to flow out of the charge chamber into the atomising means. In the shown example, the atomizing means comprise a swirl chamber with an aperture of 0.1 mm, wherein the device delivers a dose volume of 250 μl in 2-3 seconds in droplets of 10-15 μm diameter (employing an internal pressure of 4 bar).

WO 03/002045 A1 discloses a nebulizer for applying liquids on the cornea or the ocular connective tissue, wherein the nebulizer comprises a special eye adapter. The nebulizer has an energy accumulator for supplying the energy needed for the nebulization process and generates a soft mist of aerosol droplets, wherein the momentum of the aerosol cloud corresponds to a force of less than 0,00005 Newton.

Another therapeutic area pertains to the nasal cavity, i.e. there are various spray devices for generating droplets for deposition in the nose, typically finger-pump-systems for instance for the application of cold medicaments. However, there are some nasal applications which are a bit less obvious than the application of a cold medicament or a moisturizer to the nose: US 2017/0224718 A1 discloses a method for preventing or treating an olfactory triggered response within the patient wherein according to the method a thixotropic composition is applied to the nasal cavity (in particular "sprayed" to form a coating layer within at least a portion of the nasal cavity), the composition including an aqueous carrier and a viscosity agent (in the range of 2.5% to about 15% by weight within the composition) wherein the composition is configured to change from a semi-solid form (a "viscous gel") to a liquid form upon the composition being subjected to a threshold amount of shear stress and to return to the semi-solid form upon the elimination of the amount of shear stress. According to the disclosed method, the thixotropic composition can be sprayed through a standard nasal spray applicator (in particular one with a positive-displacement type pump-piston) or a squeeze type spray application, wherein the applied force (either the shear stress induced by a pump procedure or the force applied by squeezing a flexible container) is sufficient to cause at least a portion of the composition to change to liquid form which can be expelled through the outlet of the applicator. Maintaining a significant portion of the thixotropic composition in semi-solid form has advantages with regard to inhibiting microbial growth.

WO 2009/047173 A2 discloses a nebulizer for nebulizing a pharmaceutical preparation for medical aerosol therapy, in particular it discloses an inhaler for administering a propellant-free aqueous solution of a tiotropium salt from a container inserted into the inhaler. The nebulizer which is a so called soft mist inhaler (SMI) comprises a pressure generator powered by a spring. The nozzle of the nebulizer comprises two plates bonded to each other wherein at least one of the plates is microstructured, the microstructures forming a fine filter and two outlet channels resulting in two nozzle openings with a width of 2-10 microns for generating two impinging jets of the solution. The smallness of the nozzle openings results in a high flow resistance The container comprises a rigid outer casing and a bag containing multiple doses of the solution. The container or its casing is vented so that the bag can collapse when withdrawing solution. The container may be constructed as described in WO 96/06011 A1 or WO 00/49988 A2.

WO 2010/094305 A1 discloses a nebulizer for nebulizing a liquid (especially water-based or ethanol-based solutions). A container can be inserted into the nebulizer. The container comprises a rigid outer casing and a collapsible bag containing multiple doses of the liquid. In order to avoid any undesired formation of vapor or gas bubbles in the bag when withdrawing liquid form the bag, the container can be pressurized by gas pressure in the casing to facilitate collapsing of the bag and withdrawal of liquid. However, this pressurization may lead to undesired leakage from the container during non-use, even if an additional valve is provided between the container and a pressure generator or fluid pump of the nebulizer. Further, the pressurization may significantly vary due to significant increase of the gas volume during liquid withdrawal and, thus, result in significant variation of the respectively withdrawn doses of liquid.

WO 2016/012102 A1 discloses a cartridge for storing a drug solution or suspension within a nebulizer. The cartridge contains multiple doses of the liquid drug and can be inserted into the nebulizer. The cartridge comprises a rigid outer casing and either a collapsible bag or a moveable stopper. The nebulizer comprises further a mechanism to help collapsing the bag or moving the stopper or pressurizing the liquid in the cartridge, wherein the liquid is pressurized essentially only during withdrawal of liquid by applying an air pressure. In one embodiment, the cartridge comprises a pump piston for pressurizing air and a return spring for returning the pump piston, the pump piston being actuated by an actuation element formed by a housing part of the nebulizer and engaging through an opening in the bottom of the cartridge. In another embodiment, the cartridge comprises a casing forming a cylinder into which a pump piston engages wherein the pump piston is connected with the housing part of the nebulizer. An exact match of the nebulizer's pump piston with the cartridge cylinder or of the actuation element with the opening in the bottom of the cartridge is required, and insertion of the cartridge may be problematic. Further, the air pressure and, thus, the pressurization may significantly vary due to significant increase of the air volume in the cylinder when decreasing the liquid volume.

This dependency of the pressurization on the increasing air volume in a container is also characteristic for the nebulizer disclosed in WO2017/129477 A1, wherein the nebulizer comprises an air pump formed by a bellows for temporarily pressurizing the liquid in the container to help a liquid pump withdrawing the liquid from a collapsible bag in the container.

WO 99/007340 A1 and US 2003/0064032 A1 disclose aqueous aerosol preparations containing biologically active macromolecules (insulin is especially described for an example) for producing inhalable aerosols when used with a mechanical nebulizer as disclosed in WO 97/12687 (a predecessor of the nebulizer disclosed in WO 2009/047173 A2) without propellant gases. There is a note that the dynamic viscosity of such aerosol preparations should not exceed $1600*10^{-6}$ Pascal seconds (1.6 centiPoise), in order for the inhalable fraction of the generated spray to be in an acceptable range, i.e. the dynamic viscosity of a preparation for nebulization with such an SMI should not be much higher than the viscosity of water (1.5 centiPoise at 5° C. or 1.0 centiPoise at) 20° ° C. It is suggested to add ethanol to the medicament solution in order to reduce the viscosity of the solution, wherein the amount of ethanol in the aqueous formulation can be up to 50%.

Indeed, quick tests with SMIs similar to those disclosed in WO 2009/047173 A2 have reveal that they cannot be used for spraying liquids with dynamic viscosities which are permanently much above the viscosity of water. This is due to the large energy required to force liquids through a microstructure nozzle. The energy in the tested SMIs (type "Respimat®", distributed by Bochringer Ingelheim) is supplied by a spring with a mean force of 45N (the use of other springs with mean forces ranging from 30N to 120N is also possible), resulting in a device designed for nebulizing aqueous drug solutions, i.e. solutions with dynamic viscosities close to 1 centipoise at room temperature.

The method of atomisation in the Respimat®-type SMI is the Double Jet Impinger where two jets of liquid collide to form a sheet of liquid, which in turn breaks up into droplets via the formation of ligaments. The velocity and diameter of the jets determines the sheet thickness and hence the droplet sizes. For inhalation these droplets must be close to 5 microns (μm; micrometer) and below. The nozzle exit channels have typically a hydraulic diameter of 5 to 15 microns.

The energy or pressure required for any given flow rate is proportional to the dynamic viscosity. If the drug dynamic viscosity is doubled, the pressure in the system needs to be doubled for the same flow rate or same delivered dose at the same required spray time (in particular the pressure is increased by increasing the spring force). For instance oils cannot be sprayed at all with the Respimat®, as they tend to have dynamic viscosities of 10 centiPoise and above. When (in the quick test) for instance silicone oil (having a viscosity of 55 centiPoise) has been tested with the SMI, no droplets have been released from the nozzle (the oil only wells up at the nozzle openings).

Generally, nebulising pharmaceutical liquids, in particular aqueous solutions, is an established route of administering a medicament to a patient, especially in case of treating lung diseases. However, a large proportion of new drug candidates are poorly soluble in water, and therefore they are usually not considered as candidates for an inhalation therapy using nebulizers.

A poor solubility in water (if not, as for instance in case of some small molecule entities, compensated by good permeation properties) often means that the respective drug has a poor bioavailability. For administration via the oral or via the intravenous route, for some drugs nanoparticulate formulations have been developed for providing high drug concentrations with low toxicity ("Nanocrystal technology, drug delivery and clinical applications" by J. Junghanns and R. Müller, International Journal of Nanomedicine 2008:3(3), page 295-309). For bioavailability suspensions of drug crystals in water or aqueous solutions are formed. When working with suspensions issues regarding the stabilization of the dispersed particles (i.e. prevention of particle growth or agglomeration, prevention of sedimentation etc.) and regarding changed flow characteristics (increase in viscosity among others) come up. Due to these issues drug suspensions would usually not be considered as suitable for being nebulized, especially not with small channel structures which can be blocked by particle agglomerates Therefore very few experiments are known regarding the nebulization of suspensions. One study has been described in the article "Production and Characterization of a Budesonide Nanosuspension for Pulmonary Adminsitration" by C. Jabobs and R. Müller in Pharmaceutical Research, Vol. 19, No. 2, February 2002, page 189-194. Herein, a suspension of only 1% budesonide (a corticosteroid used in asthma therapy) in an aqueous solution (including surfactants) has been described which was nebulized by a commercial nebulizer (Pari Inhalierboy, a table-top equipment comprising a compressor generating an air stream for nebulizing liquid medicament as a steady stream for several minutes).

US2012067343 discloses drug formulations for the administration of glucocorticosteroids by so called next generation nebulizers wherein the formulations are aqueous dispersions or suspensions of drug particles in the size range of about 1 micro to about 3 microns (an exemplary formulation is a budesonide formulation with a budesonide concentration of 0.2 mg/ml). These next generation nebulizers use meshes or membranes containing many apertures or pores and wherein the drug formulation is forced through the mesh or membrane apertures by piezoelectric or electromechanical pumping, or alternatively, wherein the mesh is vibrated to reciprocate through a pool of the formulation, to generate multiple liquid filaments with diameters approximating the mesh apertures (between 1 and 8 microns). Given examples for these next generation nebulizers are Aradigm's AerX and Essence, PARI's eFlow, Odom or TPP's TouchSpray, Respironics' Ineb and Myneb, Omron's MicroAir series and Aeogen's Aeroneb series of aerosol generators, all of which are to be use in nebulizing sessions (lasting up to a couple of minutes) (these aerosol generators generate a steady stream of aerosol and no distinctive puffs).

SUMMARY

Object of the present invention is to provide a method and/or a preferably handheld and/or portable system of a nebulizer and a container which is suitable for nebulizing a broader range of fluids than just water and aqueous solutions.

In particular object of the present invention is to provide a system wherein withdrawal of fluid from the container is facilitated—in particular for structured fluids and/or for fluids/liquids with a higher viscosity than water—, wherein the size/volume of a withdrawn dose of liquid can be kept constant (in particular, for successive/repeated withdrawals of doses from the container) and/or precise metering is supported, and/or wherein the formation of underpressure in the container can be prevented.

Fluid materials are classified broadly as simple and structured fluids. Simple fluids are materials consisting of a homogenous phase such as a pure substance or a solution (in terms of simple fluids, the invention is in particular directed to materials consisting of a homogenous liquid phase, i.e. to liquids). Materials consisting of multiple phases such as an emulsion of immiscible liquids, gas particles in foam, solid particles dispersed in a liquid, and semisolids consisting of a multiphase structure and exhibiting a complex flow behavior are called structured fluids. This is because the interactions of their constituents generally dominate their rheological behavior. However, the present invention is in particular directed to systems wherein the structured fluid only comprises liquid phases or liquid and solid phase(s), i.e. only structured fluids not containing a gas phase.

Surprisingly, it has been found that some formulations with high dynamic viscosities (some of the tested formulations even show viscosities of up to tens of thousands of centipoises) can be sprayed with an SMI/with a nebulizer comprising a fluid pump pressurizing the formulation through a nozzle with microstructured channels/with channels with diameters in the micrometer range (preferably with hydraulic diameters between 0.5-15 microns, most preferably between 4-12 microns) and that (depending on the employed pressure and channel diameters) these sprays contain sufficient particles of the correct particle size for inhalation.

The viscous formulations to be thus found sprayable were fluids which do not have a Newtonian fluid behavior (i.e. non-Newtonian fluids) wherein the fluid has a shear rate dependent or stress dependent viscosity wherein the viscosity drops at higher rates of shear velocity resp. stress i.e. wherein the fluid has a shear-thinning (pseudoplastic) behavior or is thixotrop or is a Bingham fluid. Pseudoplastic materials flow instantaneous upon application of stress but display shear thinning behavior. For a Bingham fluid a critical level of stress must be attained in order to initiate the flow, wherein the material behaves like a solid below this critical stress.

This is advantageous in drug delivery, as often the drug cannot be dissolved in a carrier such as water or ethanol, but can be prepared in structured fluids like emulsions or suspensions that have such a non-Newtonian behavior. The possibility of such suspensions or emulsions being sprayable with a nebulizer opens up the range of drugs that can be delivered to the lungs. Thus, the invention is in particular directed to systems wherein the nebulizer is an inhaler.

Alternatively, the invention is in particular directed to systems wherein the nebulizer is a device for applying fluids to the cornea of the eye or to the connective tissue of the eye, i.e. a nebulizer/an atomizer for ophthalmological administration. The possibility of structured fluids being sprayable with a nebulizer opens up the range of formulations that can be delivered to the eye by nebulization (leading to a better distribution of the formulation in the eye than the application as droplets or rubbed-in salves and/or to a more convenient and thus better adhered to way of application as the application as droplets or rubbed-in salves feels unpleasant, not just because of the local pressure exerted on the surface of the eye):

In ophthalmology it is often desirable to apply viscous formulations like salves or gels to the eye (for instance when treating the Sicca syndrome), because due to their longer retention time the viscous formulations result in a better bioadhesion (compared to easy flowing liquids like aqueous solutions). In particular advantageous is the application of pseudoplastic fluids: The contact time in the eye is enhanced due to the high viscosity, but it causes little or no (mechanical) irritation in the eye as the fluid is shear thinned due to the pressure exerted by the movement of the eye lid and thus well distributed in the eye. Examples for such an ophthalmologic formulation with pseudoplastic behavior are formulations containing hyaluronic acid.

Additionally, the possibility of administering o/w-emulsions or suspensions to the eye opens up the possibility of administering drugs with poor solubility in water/water-insoluble drugs to the eye.

The shear forces in the nozzle channels of the nebulizer according to the invention (in particular an SMI/“Respimat®-type” nebulizer) are very high. The shear forces occur when the fluid (or liquid) travelling through the middle of the channels moves in relation to the channel walls (and are thus defined by the size of the channels and the velocity of the fluid, the velocity being dependent on the pressurization of the fluid). The shear rate is defined as the measure of the extent or rate of relative motion between adjacent layers of a moving fluid.

Surprisingly some highly viscous emulsions with dynamic viscosities of about 10000 centipoise can be used with the nebulizer suggesting the dynamic viscosity is reduced to near 1 centipoise in the microstructures/nozzle channels.

Emulsions contain droplets of an immiscible fluid suspended in a carrier liquid, i.e. they are fluids wherein a second liquid is suspended as droplets in a first liquid. For instance an ‘oil in water’ emulsion (o/w emulsion) has oil droplets suspended in water and examples include hand creams and milk. ‘Water in Oil in Water’ emulsions (w/o/w emulsion) also exist where water particles are suspended in oils particles, which in turn are suspended in water. More complex emulsions can be made with any number of liquid types such as body lotions with sometimes dozens of different liquids mixed together in a stable emulsion. Most man made emulsions will also include an emulsifier, as often an emulsifier (=surfactant=surface active agent) is needed to disperse two immiscible liquids, like a polar and a nonpolar liquid. In the emulsion, the surfactant will mainly be found on the interface of the inmiscible liquids, lowering the interfacial tension and thus lowering the interfacial energy and increasing its stability.

Typically emulsions would be thermodynamically unstable (the dispersed droplets tend to flow together to reduce the surface energy=product of surface and surface tension) and are stabilized by addition of surface active agent. The surface active agent can be an ionic or a nonionic stabilizer (or a combination of both).

So called micro-emulsions are thermodynamically stable, because they comprise tensides/surfactants reducing the surface tension/interfacial tension (almost down to zero). In addition, emulsions can be kinetically stabilized by matching the densities of both phases, increase of viscosity or reduction of the droplet size.

Many emulsions change viscosity under high shear forces: Typically, the viscosity of a concentrated emulsion is a function of the rate of shear, decreasing with an increase in the rate or shear and approaching an asymptote as the rate of shear is increased further. Over wide ranges the relation between shearing stress and rate of shear is linear.

In particular, emulsions comprising a carrier liquid (like water or ethanol) which has a low viscosity (i.e. not exceeding 1.6 centipoise) are used for nebulization with the system according to the invention. Tested "water in oil"-type of emulsions were not sprayable with the nebulizer of the system, at least not when the respective oil was not sprayable with said nebulizer.

This is backed up by the following idea on the limit of a possible shear rate dependency: When a pressure dependency exists for emulsions and suspensions which are based on a carrier liquid for which the viscosity does not depend on the shear rate, it is to be expected that the viscosity of the structured fluid cannot be reduced to values below the viscosity of the carrier fluid.

Accordingly, the fluid/emulsion preferably does not comprise or does only comprise a small fraction of a component which increases the base viscosity/non-shear-rate-dependent viscosity i.e. preferably the base-viscosity is mainly determined by the carrier liquid. The acceptable amount of the fraction depends on its (individual) effect on the base viscosity/on its (individual) interaction with the carrier liquid. (The "acceptable amount" is such an amount which does not result in a base viscosity above 1.6 centipoise for the out phase wherein mainly data viscosities at typical laboratory conditions, i.e. at room temperature, are considered in general).

Such a component increasing the base viscosity was found to be glycerin—a humectant (used for instance in hand lotions) that works to moistures the skin and is also used for thickening purposes in the formulation of lotions. In particular, the fluid to be nebulized with the system according to the invention comprises less than 15% glycerin (increasing the base viscosity of water to 1.65 centipoise), in particular less than 10% glycerin or most preferably less than 1% or no glycerin.

Quick tests with various commercially available body lotions not containing glycerin proofed to be sprayable with the nebulizer of the system, at least if diluted with 30% to 50% water and/or ethanol. Preferably, an emulsion does not contain more than 30% oil. (for example, a typical body lotion contains 5% oil).

Suspensions contain particles of an insoluble material (or material of poor solubility) suspended in a carrier liquid, i.e. they are similar to emulsions, but contain solid particles instead of the liquid droplets dispersed in the carrier fluid. Experiments show that suspensions of dynamic viscosities of 100 centipoise can be sprayed in a system according to the invention. In particular, suspensions comprising a carrier liquid (like water or ethanol) which has a low viscosity (i.e. not exceeding 1.6 centipoise) are used for nebulization with the system according to the invention.

Preferably, the suspension to be nebulized according to the present invention is a so-called nanosuspension, i.e. the particles contained in the fluid are at least in one direction smaller than 1 micron (at least regarding their majority). For medicinal applications, the nanoparticles are produced in a milling process from coarse crystals. Depending on the milling conditions and milling times various ranges can be generated for the distribution of the grain size. (for instance 0.1 μm to 0.5 μm). In suspension the particles normally are stabilized in a colloidal dispersion (the particles typically having a low solubility in the carrier liquid), wherein surfactant aids can be used for stabilizing the particle suspension (very similar to the stabilization in emulsions, but with the additional aspect that by use of specific surfactants or polymeric stabilizers surface properties like the wettability of the particles can be modified; the addition of a peptizer for instance may serve to prevent the coagulation of a colloid suspension).

Besides classical suspensions and emulsions there is another group of fluids which can exhibit a similar rheologic behavior: Liposomal fluids which are in particular aqueous formulations containing liposomes, lipid droplets (nanoemulsions in which lipid monolayers enclose liquid lipid cores) or lipid nanoparticles (lipid monolayers enclosing solid lipid cores, i.e. a liposomal fluid can also be an emulsion or suspension—or both in case of the core consisting of solid and liquid lipids). A liposome is a particle or droplet formed by a lipid layer enclosing an aqueous core (you could say that a formulation containing such liposomes is a sort of w/o/w-emulsion).

In therapeutic applications the core of the liposomes or of the lipid droplets or particles can comprise a dissolved (/embedded) drug/(pharmacologically) active ingredient, i.e. like for nanosuspensions the core of the lipid droplets or particles can be drug loaded. Using liposomal fluids or nanosuspension offers various additional pathways in therapeutics: encapsulation of proteins, macromolecules, localized drug uptake/passive and active drug targeting, the possibility of sustained/controlled drug delivery etc. In particular the liposomal fluids comprise a physiological lipid like phospholipids which are similarly also found within the human body, for instance as a lung surfactant. Typically liposomes are produced from lecithin which is obtained from eggs or soy. An alternative to lecithin is dipalmitoylphosphatidylcholin (DPPC) which is part of the pulmonal surfactant and thus a substance produced naturally in the human body. A liposomal fluid for therapeutic use (for instance for inhalation) can for instance comprise water as a carrier liquid, a hydrophilic or lypophilic active ingredient, phospholipids, a buffer and preservatives.

In ophthalmology, the application of liposomal fluids (even without additional drugs) is of particular interest (for example) when treating evaporative dry eye (EDE) symptoms. EDE accounts for approximately 80 percent of dry eye cases and its' cause is a deficiency or instability of the lipid layer of the tear film which normally acts as a seal for the watery/aqueous layer, preventing it from evaporating (the third layer of the tear film being the mucin layer which ensures the contact of the water with the surface of the eye). An exemplary fluid for treating EDE symptoms contains soy lecithin (dispersed in water), a phospholipid, which forms microscopic spherical liposomal vesicles in the fluid. Soy lecithin is an emulsifier, which due to its bipolar nature enables the water and oil layers of the eye to work together (phospholipids can form either liposomes, bilayer sheets, micelles, or lamellar structures, depending on hydration and temperature.). The liposomal formulation acts twofold: The water contained adds to the aqueous layer of the eye (i.e. moisturizes the eye) and the delivery of phospholipid to the eye helps to repair the lipid layer, thereby addressing the lipid instability that causes EDE.

According to one aspect of the invention, a system comprising a nebulizer for nebulizing the fluid and a container containing the fluid, in particular multiple doses of the fluid, is provided, wherein the nebulizer comprises a fluid pump for withdrawing a dose of the fluid from the container and pressing the respective dose with an operational pressure of 5 to 250 MPa, in particular 10 to 50 MPa, through a nozzle with at least one channel, preferably at least two channels, having a hydraulic diameter in the range of 3 to 20 microns, in particular 4 to 12 microns, most preferably 5 to 8 microns and wherein the fluid has a viscosity at rest (at room temperature) of more than 1.7 centipoise (or more than 2 centipoise), preferably more than 10 centipoise (and/or in particular up to 300000 centipoise), and wherein the fluid has a shear-thinning behavior (i.e. wherein the viscosity of the fluid decreases for increased rates of shear). In particular the nozzle is formed by a microstructured component, preferably wherein at least two nozzle channels generate impinging jets of fluid. Preferably, the shear-thinning behavior is such that the viscosity of the fluid is reduced to 200 centipoise or less, most preferably to 10 centipoise or less, for shear rates of up to 1000 per second (1000 $s^{-1}$). Preferably, for fluids with a viscosity at rest of $\eta_0>160$ centipoise, the shear-thinning behaviour is such that the viscosity decreases from a viscosity value $\eta_0$ at rest to a viscosity value $\eta_s$ when the shear rate is increased to 1000 $s^{-1}$, wherein $\eta_s$ is smaller than $\eta_0*10^{-x}$ (i.e. decreases by a factor of $10^{-x}$ wherein x is a numeral of at least 2 or a numeral bigger than 2).

In particular, the present invention relates to a nebulizer for nebulizing a fluid and preferably a medicament container containing the fluid in a variable or collapsible or compressible volume formed or limited in particular by a collapsible bag or moveable fluid piston or any other construction comprising a compressible inner cavity or inner container forming an inner cavity. [In one type of embodiment, the container comprises an inner container (which is flexible/collapsible, preferably in form of a collapsible bag, foil construction or the like) and a surrounding more rigid structure like a casing; in another type of embodiment, the container comprises a rigid structure or casing and a fluid piston moveable within the casing for forming a variable or collapsible volume for the liquid.]

Preferably, the nebulizer comprises a housing part which can be detached or opened for inserting the container. The nebulizer comprises a fluid pump or pressure generator for drawing the fluid (in particular a metered dose of fluid) from the container and/or for dispensing the dose of fluid, in particular without the use of a propellant for pressurizing the fluid. In particular, the container contains multiple doses of the fluid.

According to an additional aspect of the present invention, the nebulizer or its container comprises preferably an air pump for pressurizing the fluid in the container to help withdrawing the fluid in doses from the container. Preferably, a pressure pulse—in particular provided or generated by the nebulizer or air pump—acts on the variable volume or the fluid in the container at the beginning and/or during the tensioning of the nebulizer and/or withdrawal of fluid from the container.

Especially for viscous fluids, this pressurization of the container helps spreading the fluid within the nebulizer so that the fluid reaches the nozzle where shear forces effect the fluid eventually.

Preferably, the air pump pressurizes the container and/or fluid in the container only temporarily, in particular only when the nebulizer is cocked or tensioned or loaded (i.e. readied for nebulizing a dose of fluid) and/or when fluid is drawn out of the container. Thus, any undesired leakage of fluid from the container can be prevented or at least minimized and/or any (additional) valve between the container and the fluid pump or pressure generator of the nebulizer can be avoided. This allows a simple construction.

Further, the temporary pressurization of the fluid in the container can prevent the formation or growing of any gas bubble within the fluid/container. This supports precise metering and/or allows minimization or reduction of the total volume of fluid initially provided in the container.

Preferably, the air pump comprises or forms a piston/cylinder arrangement for temporarily pressurizing air in the container to help withdrawing the fluid in doses from the container. This allows a very simple construction of the air pump.

Optionally, the nebulizer or air pump comprises a pump piston which is driven by the container for pumping air into the container. This allows a very simple construction and/or use of known containers.

According to an alternative embodiment, the container may form a pump piston of the air pump for pumping air into the container. This allows a very simple construction.

Preferably, the pump piston cooperates with the housing part of the nebulizer or with a cylinder or insert associated to or held by the housing part. This allows a very simple construction and requires only minor modification of known nebulizers.

Preferably, the air pump is arranged in, fastened to or formed by the housing part of the nebulizer that can be detached or opened for inserting or replacing the container.

Optionally, the container is moveable relative to the air pump during tensioning or cocking or loading the nebulizer or withdrawing a dose of fluid from the container and/or during nebulizing or dispensing a dose of fluid. This relative container movement is preferably used for actuating the air pump and/or for only temporarily pressurizing the fluid in the container and/or only temporarily connecting the air pump to the container (preferably, the air pump is not connected to the container in a non-tensioned or non-loaded state of the nebulizer). This allows a very simple and reliable construction.

Optionally, the air pump is fluidically connectable to a bottom or axial end of the container, preferably opposite to an outlet of the container and/or via a venting hole of the container. This allows a very simple construction or integration in known nebulizers.

Preferably, the nebulizer or air pump comprises a control valve limiting the air pressure acting on the fluid in the container to a maximum value above the ambient pressure independently from a filling level of the container with the fluid. This supports or allows precise metering of the fluid and/or prevents any undesired leaking of fluid which could occur in case of very high pressures acting on the fluid.

Preferably, the nebulizer or air pump comprises an inlet valve preventing any underpressure in the air pump or its pump chamber. This supports precise metering and can prevent any negative force acting on the fluid in the container during nebulization.

Preferably, the control valve and the inlet valve are formed by same valve or valve element. This allows a very simple construction.

According to another aspect of the invention (which can be considered separately from or in combination with the afore mentioned aspects), a method for nebulizing a fluid, in particular a liposomal fluid, made from at least two components is provided, wherein the fluid is nebulized from/with a system of a cartridge and a nebulizer, wherein the cartridge comprises a port for fluidically connecting the cartridge to the nebulizer, and wherein the cartridge comprises at least two chambers/inner volumes each containing one of the at least two components. In a storage situation/ before preparing the nebulizer for use with the cartridge (in particular before fluidically connecting the cartridge and the nebulizer), the at least two chambers are fluidically separate. In particular, the first chamber contains as a first component a preferably ethanolic solution containing lipids or a powder comprising lipids and the second chamber contains an aqueous liquid as a second component, wherein a liposomal medicament/pharmaceutical product containing liposomes is fabricated/produced by combining/mixing the two components.

BRIEF DESCRIPTION OF THE DRAWINGS

Further advantages, features, characteristics and aspects of the present invention will become apparent from the claims and the following description of preferred embodiments with reference to the drawings. It shows:

In the Figures, the same reference numerals are used for identical or similar parts, resulting preferably in corresponding or comparable properties and advantages, even if the associated description is not repeated.

DETAILED DESCRIPTION

Figure 1:
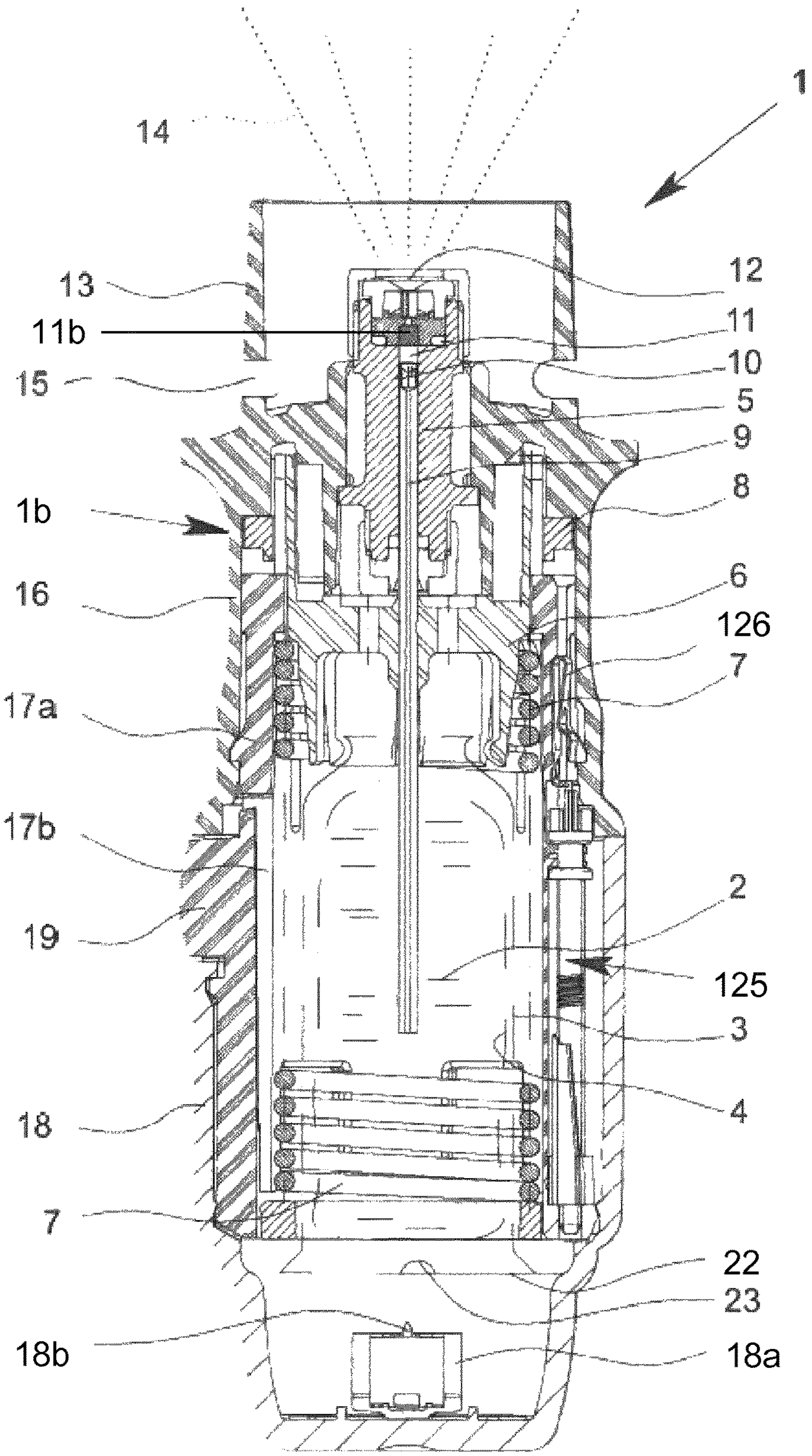
FIG. 1 a schematic section of a known nebulizer in a non-tensioned state.
Figure 2:
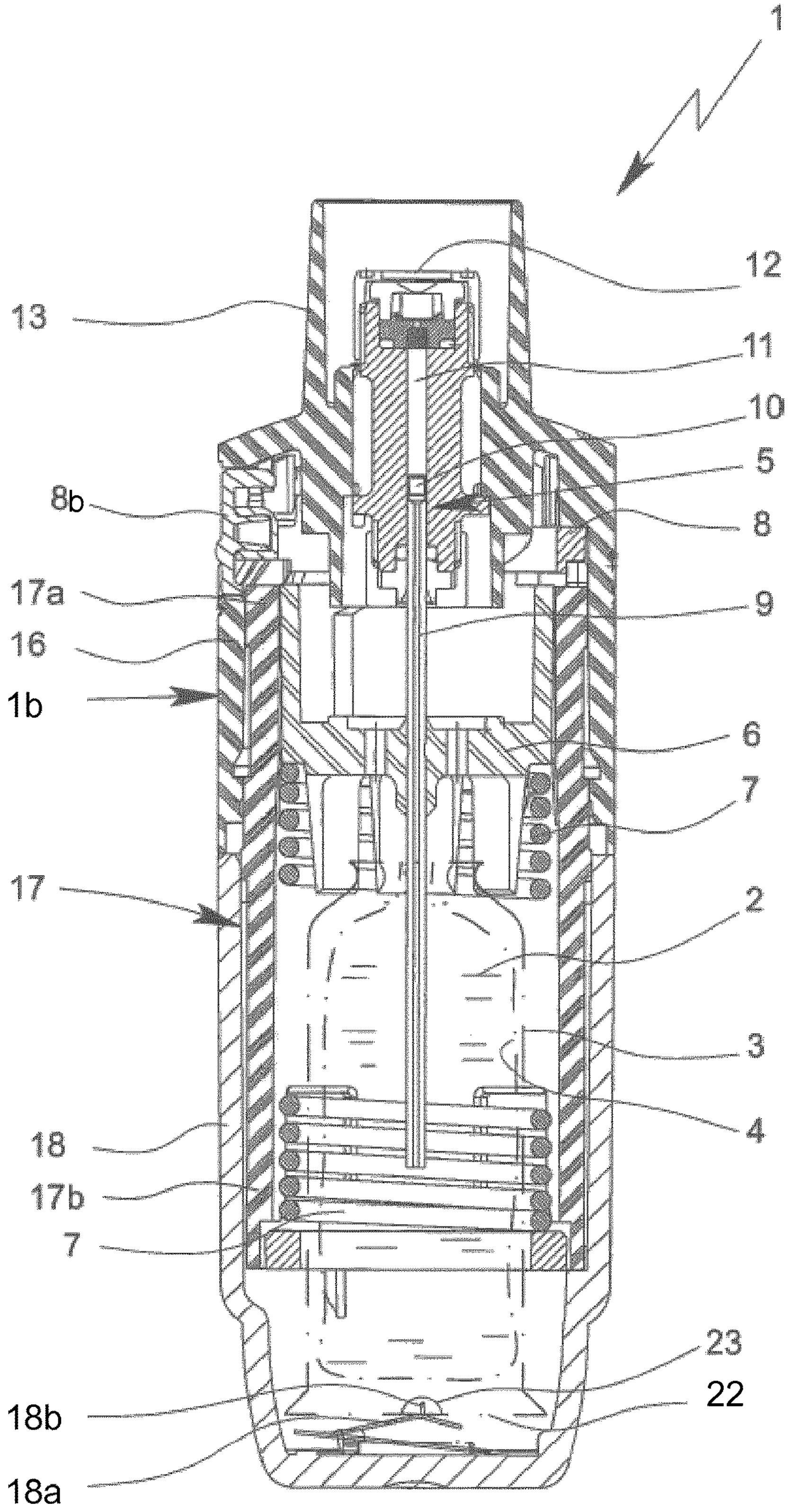
FIG. 2 a schematic section, rotated 90° compared with FIG. 1, of the nebulizer in a tensioned state.

FIGS. 1 and 2 show a nebulizer 1 known for atomizing a in particular aqueous liquid, particularly a highly effective pharmaceutical composition, medicament or the like, shown in a non-tensioned state (FIG. 1) and in a tensioned state (FIG. 2). The nebulizer 1 is constructed in particular as a portable inhaler and preferably operates only mechanical and/or without propellant gas.

According to the invention, the nebulizer can surprisingly be used not only for nebulizing classical liquids of low viscosity or especially aqueous solutions, but also for nebulizing a broader range of fluids 2, in particular fluids 2 comprising a liquid phase (at least one liquid phase) and having a base viscosity of up to 1.6 centipoise or a viscosity which can be reduced down to 1.6 centipoise or below due to shear rate dependencies.

When the fluid 2, more particularly a pharmaceutical composition, is nebulized, an aerosol 14 (FIG. 1) is formed or dispensed, which can be breathed in or inhaled by a user. Usually the inhaling is done at least once a day, more particularly several times a day, preferably at set intervals, depending on the complaint or illness from which a patient is suffering.

The nebulizer 1 is provided with or comprises an insertable or replaceable container 3 containing the fluid 2. The container 3 thus forms a reservoir for the fluid 2, which is to be nebulized.

Figure 4:
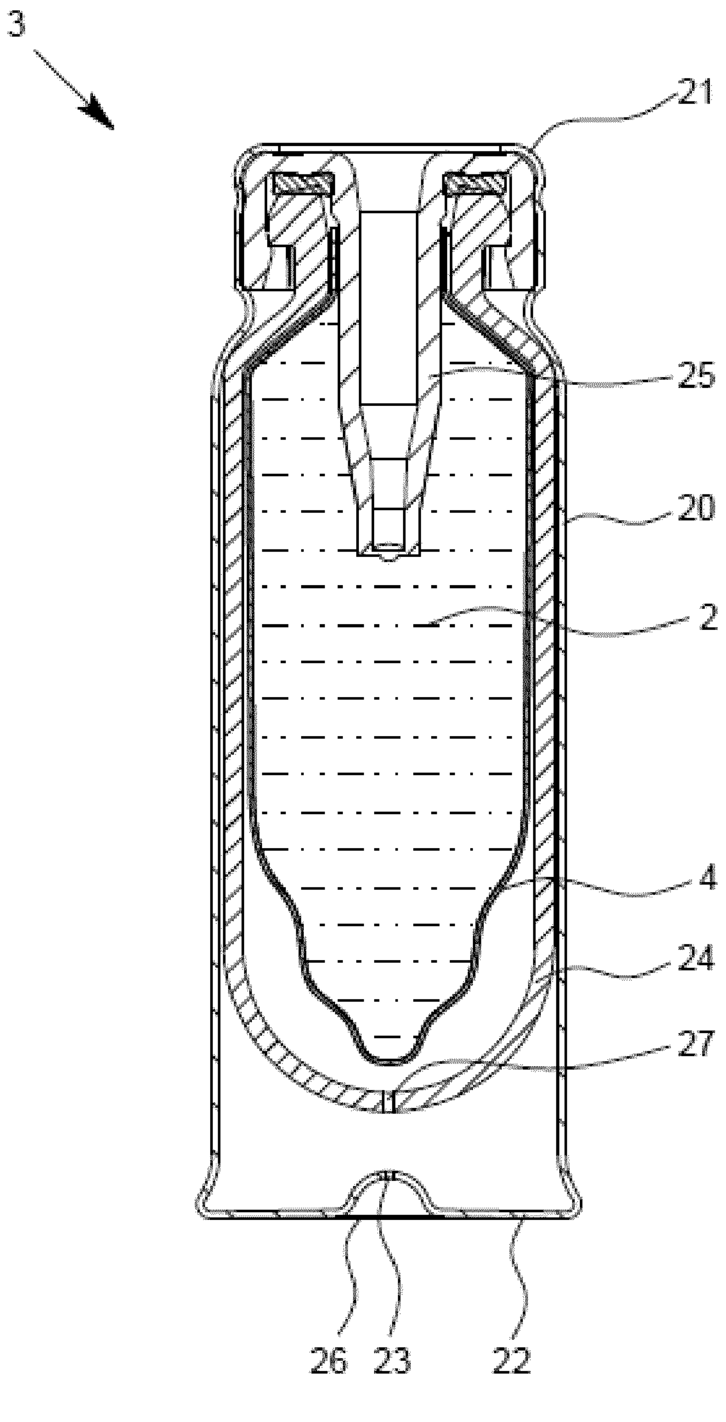
FIG. 4 a schematic section of an embodiment of a known container for the nebulizer.

The container 3 is shown in FIGS. 1 and 2 only schematically and in the section of FIG. 4 in more detail.

The container 3 is preferably substantially cylindrical or cartridge-shaped and once the nebulizer 1 has been opened the container 3 can be inserted therein preferably from below and changed if desired.

Preferably, the container 3 contains multiple doses of fluid 2 or active substance in particular sufficient to provide at least 100 or 150 and/or up to 200 or more dosage units or doses, for example, i.e. to allow at least 100 and/or up to 200 sprays or applications. The container 3 holds preferably a volume of about 0.5 to 30 ml, preferably 2 to 20 ml.

Further, the number of doses contained in the container 3 and/or the total volume of the fluid 2 contained in the container 3 can vary depending on the fluid 2 or respective medicament and/or depending on the container 3 and/or depending on the necessary medication or the like.

Preferably, the nebulizer 1 is adapted to nebulize a dose of 1 to 80 microliters of fluid 2, even more preferably a dose of more than 5, 10 or 20 microliters or of about 50 microliters, within one actuation/use of the nebulizer 1/within one spray/aerosol delivery/dispensation.

Preferably, the total number of uses of the nebulizer 1, which can be used with the same nebulizer 1, is restricted. In case the container 3 can be replaced or exchanged (wherein the nebulizer 1 or a holder 6 therein for holding the container 3 is constructed so that the container 3 can be released or exchanged), the number of containers 3 which can be used with the same nebulizer is therefore restricted, for instance to a total number of three, four, five or six containers 3. Details on such a restriction are shown in WO 2012/162305 A1 which discloses a nebulizer for successive use with multiple containers wherein the nebulizer comprises a mechanism to restrict the total numbers of containers to be used with the nebulizer.

Preferably, the nebulizer comprises a locking device 126 which locks the nebulizer against further use when a certain number of actuations or operations or discharged doses has been reached or exceeded. In particular if used with a comparatively large container 3, the number of actuations or operations corresponds to the number of doses to be dispensed from one container 3.

The nebulizer 1 comprises a fluid pump 5 (which is part of or forming a pressure generator, i.e. part of the delivery mechanism of the nebulizer 1), for conveying and nebulizing the fluid 2, particularly in a preset and optionally in an adjustable dosage amount. In particular, fluid pump 5 withdraws or sucks fluid 2, namely a dose of the fluid 2, from the container 3 or its bag/volume 4, preferably when cocking or tensioning or loading the nebulizer 1. Then, the withdrawn fluid 2 or dose of fluid 2 is dispensed, in particular pressurized and/or nebulized, preferably in a second step after the tensioning or loading process. In particular, the nebulizer 1 comprises an energy store (preferably a drive spring 7) which is loaded (preferably tensioned) during the loading or tensioning process and the energy is released for nebulizing the fluid 2 or dose of fluid 2 which has been drawn into the nebulizer 1 during the tensioning or loading process. Thus, the normal use of the preferred nebulizer 1 encompasses the loading process and the dispensing process.

The nebulizer 1 or pressure generator/fluid pump 5 comprises preferably a holder 6 for holding the container 3, the drive spring 7 associated to the holder 6, only partly shown, and/or a blocking element 8 preferably in form of or with a button 8*b* for preferably manual actuation or depressing. The blocking element 8 can catch and block the holder 6 and can be manually operated to release the holder 6 allowing drive spring 7 to expand.

The nebulizer 1 or pressure generator/fluid pump 5 comprises preferably a conveying element, such as a conveying tube 9, a non-return valve 10, a pressure chamber 11 and/or a nozzle 12 for nebulizing the fluid 2 into a mouthpiece 13.

The completely inserted container 3 is fixed or held in the nebulizer 1 via the holder 6 such that the conveying element fluidically connects the container 3 or its bag 4 to the nebulizer 1 or pressure generator/fluid pump 5. Preferably, the conveying tube 9 penetrates into the container 3 and/or bag/volume 4.

When the drive spring 7 is axially tensioned in the tensioning process or during cocking, the holder 6 with the container 3 and the conveying tube 9 are moved downwards in the drawings and fluid 2 is withdrawn or sucked out of the container 3 into the fluid pump 5 or its pressure chamber 11 through the non-return valve 10. In this state, the holder 6 is caught by the blocking element 8 so that the drive spring 7 is kept compressed. Then, the nebulizer 1 is in the cocked or tensioned state.

During the subsequent relaxation in the nebulization process after actuation or pressing of the blocking element 8 (either directly or by way of pressing an associated button 8*b*) the fluid 2 in the pressure chamber 11 is put under pressure as the conveying tube 9 with its now closed non-return valve 10 is moved back in the pressure chamber 11, here in the drawings upwards, by the relaxation or force of the drive spring 7 and now acts as a pressing ram or piston. This pressure forces the fluid 2 through the nozzle 12, whereupon it is nebulized into the aerosol 14, as shown in FIG. 1, and, thus, dispensed.

The nozzle 12 is preferably formed by a microstructured component. In order to produce inhalable aerosols most nebuliser designs require very small nozzle structures which are often produced by so-called microsystem technologies such as lithographic manufacturing methods from semiconductor production or spark erosion or laser drilling techniques.

Figure 3:
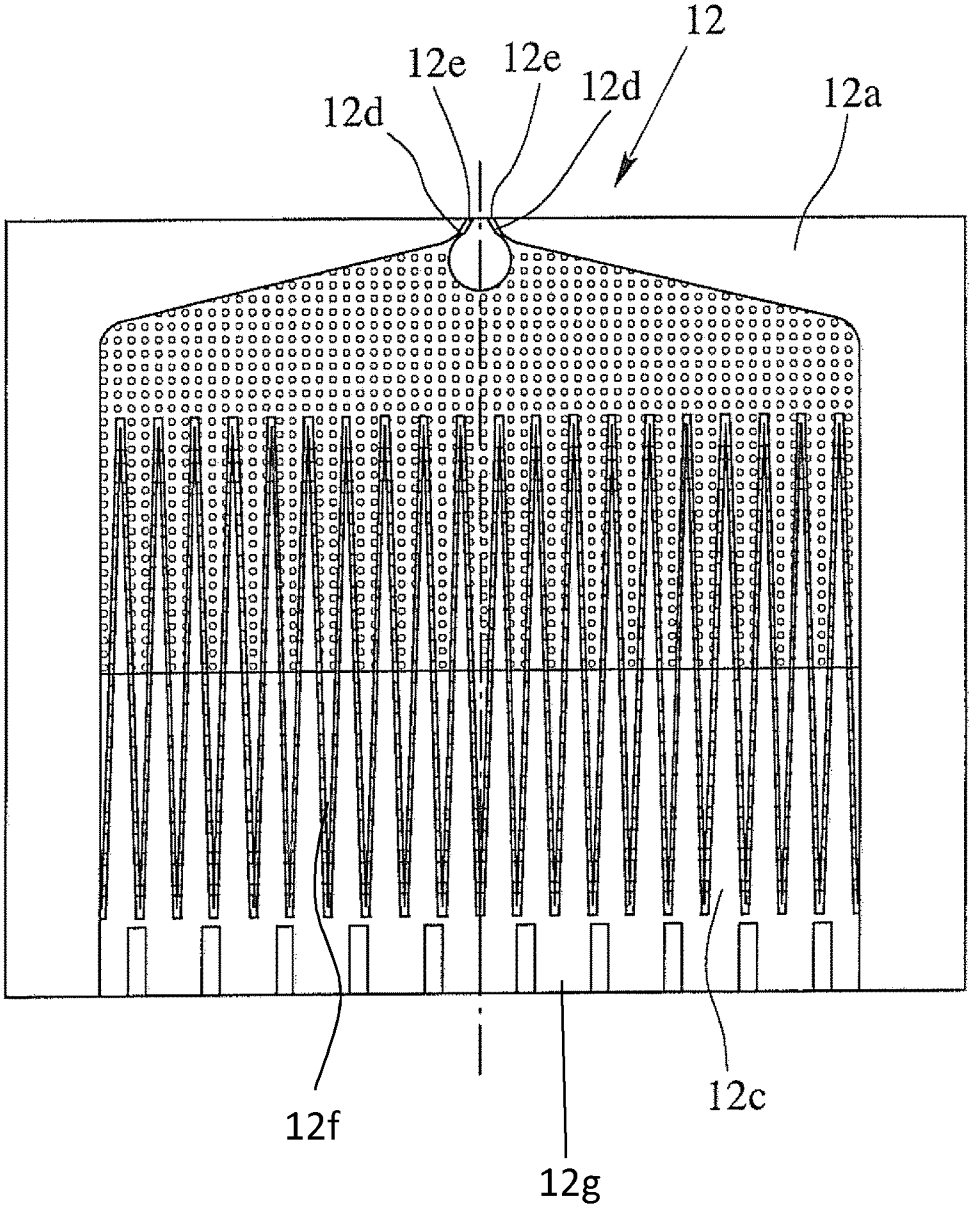
FIG. 3 is a schematic plan view of a microstructure or a section through a microstructured component forming a nozzle for installation in a nebuliser.

A microstructured component or nozzle 12 that can be used for insertion in the specific embodiment is shown in FIG. 3. The shown nozzle 12 is made up of a microstructured plate 12*a*. preferably of silicon, and a cover plate 12*b*, preferably made of glass, that covers the structures. In the shown embodiment, the nebulisation of the fluid with the nebuliser is preferably based on the high speed impact of two jets of fluid: Jets of fluid emerge from the preferably two nozzle channels 12*d* or from the associated nozzle openings 12*e*, directed so as to meet at a defined angle, and are nebulised by the forces that act during the impact.

Preferably, the nebulizer 1 comprises means for filtering particles upstream of the nozzle openings 12*e*, in order to keep the nozzle openings 12*e* free from obstruction and thus to ensure operational capability of the nozzle 12.

Most preferably, the microstructured component or nozzle 12 comprises both the nozzle openings 12*e* and also a fine filter 12*f*. In the shown embodiment, the nozzle 12 comprises a microstructure which (viewed along the flow direction of the fluid) form inlet openings 12*g* followed by in inflow region 12*c*, a fine filter 12*f* designed as a flow filter along the direction of flow and then the nozzle channels 12*d* (which form the nozzle openings. The filter action is achieved by a special arrangement of solid struts and passages. Particularly preferred is a zigzag arrangement of rows of struts with very fine passages having a manufactured rectangular profile. Preferably, the widths of the passages is smaller than the width of the nozzle openings 12*c*.

In the embodiment shown, the dimensions of the nozzle channels 12*d* of the favoured microstructured component 12 are just a few microns. Preferably, the nozzle channels 12*d* have a rectangular profile with edge lengths of 3 to 20 microns, in particular 4 to 12 microns, most preferably 5 to 8 microns (corresponding to similar values for the hydraulic diameter). The dimensioning of the nozzle channel often depends on the volume of the dose which is to be ejected in a certain time frame. For nebulizing a volume of 50 μl within one dose and within a spray time of less than 2 s, it is suitable to enlarge the width and the height of the nozzle channels 12*d* to 11 microns to 12 microns, besides adjusting the per actuation conveyed/delivered volume as such. Generally (looking at the nebulizer of FIGS. 1 to 3), changing a set-up of a nebulizer 1 from one nebulized volume (of for instance 15 μl) to another nebulized volume (of for instance 50 μl) is a matter of adjusting the dimensions of the nozzle outlet diameter, the force of spring 7 and the cross sectional areas of the pressure chamber 11 and the piston moving therein (formed by the conveying tube 9 in this embodiment).

Accordingly, the widths of the passages of the fine filter 12*f* are also just a few microns—preferably particles up to about 2 microns in size are removed from the fluid before it enters the nozzle channels 12*d* and is later breathed in by a user of the inhaler after nebulisation. Preferably, the nozzle channels 12*d* have a length of 10 to 100 microns, in particular 20 to 60 microns, most preferably 30 to 50 microns. Preferably, the nozzle dimensions are chosen to suit the fluid to be nebulized: The flow velocity is increased for the smaller channel lengths, for smaller diameters the risks of channel blockades due to the fluid itself can be increased (in particular for suspensions, for example).

Further details of possible structures for the microstructured component or nozzle 12 or for the fine filter 12*f* installed in a nozzle assembly are disclosed in the specifications of WO94/07607A1, WO99/16530A1, WO05/000476A1, WO07/101557A2 and WO08/138936A2.

Preferably, the nebulizer comprises a filter system or pre-filter 11*b* filtering the fluid 2 before it enters the nozzle or microstructured component forming the nozzle. Preferably the filter system or pre-filter 11*f* is arranged in the fluid outlet region of the pressure chamber 11. Preferably, the filter thresholds of the pre-filter 11*f* or of individual filter components forming the filter system are of such a size that each filter lets through smaller particles than the one before it, according to the principle of size exclusion.

In the shown embodiment, the pre-filter preferably has a filtering threshold of a size a bit larger than the hydraulic diameter of the nozzle channels 12*d*, for instance a threshold of 10 microns (i.e. the filter holds back particles bigger than 10 micrometers) in case of a hydraulic diameter of 6-7 microns for the nozzle channel 12*d*. Preferably the filter consists of a material which does not chemically react with the fluid 2 or with contents of the fluid 2. In particular, the filter consists of a polyolefin, preferably polyethylene (PE) or polypropylene (PP), most preferably in sintered form.

By the arrangement of filters with a successively increasing separation level, or successively smaller pore sizes, a higher filter capacity is achieved overall, i.e. the deposition of larger quantities of particles or agglomerates of particles without complete clogging of the filters, and a more thorough filtering. The first filter installed in the flow path with the largest pore diameter traps only the large particles or agglomerates of particles, the next filter with a smaller pore diameter traps smaller particles, and so on (the passages in the fine filter 12*f* of the microstructured component forming the smallest pore diameters in the sequence of filtering components). Depending on the particle load or the freedom from particles required of the fluid or liquid that is delivered, it is also possible to incorporate additional filtering components. In this way, a fine-pored filter is not directly clogged by large particles to the point where it cannot allow any fluid or liquid at all to pass through. Further details of possible sequences of filtering components in nebulizers are disclosed in the specification WO 2012/007315.

In case the fluid 2 is a suspension of solid particles, for instance a nanosuspension, the particles are preferably designed to pass all filters of the nebulizer, i.e. the particles preferably have diameters which are smaller than the passages of the fine filter 12*f*. Preferably, the particles have a hydraulic diameter (at least regarding their majority) smaller than 5 micron. Most preferably, the particles have a major cross section which is less than the width of the passage of the fine filter 12*f* (for instance a diameter of 2 microns or less), with the largest cross sectional diameter being smaller than the height of the passage of the fine filter 12*f* (for instance 8 microns or less). Even more preferably the particles in suspension are nanoparticles.

Preferably the particles have only a low tendency for forming aggregates (otherwise the reusability of the nebulizer in repeated actuations would be reduced due to a quick exhaust of the filter capacity). Generally, it is to be expected that the tendency for agglomeration increases with the concentration of the nanoparticles. Therefore, the significance of the dimensioning of the filter stages and filter capacities increases with the concentration of the suspended particles.

One possibility to reduce the tendency for forming agglomerates is the addition of a dispersion aid/surfactant/wetting agent to the fluid 2 (i.e. preferably the fluid 2 comprises a dispersion aid in addition to the nanoparticles), in particular wherein the dispersed particles are (highly) wetted with the dispersion aid. For instance, due to such a dispersion aid a solvate shell is formed around the dispersed particles, securing a distance between neighbouring particles. Ions encased in such solvate shells additionally result in an electrical repulsion. Tensides can be used for enhancing the wetting of the particles with the dispersion aid, i.e. preferably the fluid 2 contains at least one tenside in addition to the dispersion aid.

Often the surface of the particles is negatively charged due to the adsorption of negative, non-solvated ions. This negative charge repulses neighbouring, negatively charged particles. Ions for instance in form of peptizers (multivalent anions like for instance citrate, tartrate) can be added for balancing the surface charge. The surface charge can be determined by Zeta potential measurements.

In case the fluid 2. in particular a suspension, emulsion or liposomal fluid, has a low stability (for instance when the tendency for forming agglomerates cannot be sufficiently reduced by adding a dispersion aid), the fluid 2 can be mixed/produced from several (stable) components just shortly before it is to be nebulized. For such a comparatively unstable fluid 2, a (not shown) cartridge can be used, in which the different components of the fluid 2, for instance a powder consisting of nanoparticles and a solvent, are stored in different compartments/inner volumes of the cartridge which are fluidically connected (for mixing) just shortly before the nebulizer is used with this cartridge. Examples for such cartridges are disclosed in WO 97/39831 A1 and WO 00/23037 A1. WO 97/39831 A1 discloses a cartridge with two compartments for separate storage of an active ingredient/drug and the solvent for the drug, for instance for extending the storage time of the drug. When the cartridge is inserted into a nebulizer the compartment containing the active ingredient/drug is pierced through by a cannula/hollow needle (formed for instance by an element like the conveying tube 9 of the nebulizer 1), so that the active ingredient/drug can be dissolved in the solvent.

This approach of storing different components of a fluid 2 separately and mixing them just shortly before using the fluid 2 can also be advantageous when the fluid 2 is a structured fluid, i.e. wherein the stability of the fluid 2 is also influenced by the stability of the dispersion forming the structured fluid.

In particular, it is possible to mix components of a liposomal fluid shortly or directly before use of the cartridge (container 3, not shown embodiment) with the nebulizer/before nebulizing fluid 2 from the cartridge with the nebulizer 1. Preferably, the liposomal fluid or liposomes in fluid 2 are thus formed within a chamber in the cartridge (container 3, not shown embodiment).

According to one aspect of the invention, a system of a cartridge/container 3 and a nebulizer 1 and a nebulizer for nebulizing a fluid 2 from the cartridge/container 3 is provided (preferably the fluid is a therapeutic/pharmaceutical fluid or a fluid comprising at least one drug/at least one active ingredient), wherein the fluid 2 is fabricated/produced from at least two components and wherein the cartridge comprises a closure 25/port for fluidically connecting the cartridge/container 3 to the nebulizer 1, and wherein the cartridge/container 3 comprises at least two chambers/inner volumes each containing one of the at least two components. In a storage situation/before preparing the nebulizer 1 for use with the cartridge/container 3/before fluidically connecting the cartridge/container 3 and the nebulizer 1, the at least two chambers are fluidically separate. In particular, the first chamber contains as a first component a preferably ethanolic solution containing lipids or a powder/particles comprising lipids and the second chamber contains an aqueous liquid as a second component, wherein a liposomal medicament/pharmaceutical product containing liposomes is fabricated/produced by combining/mixing the two components.

Preferably (in this mixing approach), at least one of the at least two components which are mixed to form fluid 2 is solid during storage, preferably in form of a powder and/or, particularly preferable, freeze-dried or lyophilized particles/liposomes. Preferably, an active ingredient/drug is embedded or encapsuled in the dry particles/liposomes and/or in the membrane of the liposomes. The powder or particles may comprise one or more additives like lactose, mannitol, lecithine, cholesterol, polyethyleneglycol or glycerin or the like.

For example one or more lipophilic/hydrophobis active ingredients (drugs) are embedded or encapsuled in the liposomes or in the membrane of the liposomes (for example a glucocorticoide like Budesonide, Ciclesonide, Fluticasone or Beclometason).

The second of the at least two separately stored components is a fluid, in particular water or a solvent containing water. The second component can comprise (additionally or alternatively) one or more lipophobic/hydrophilic active ingredients (drugs) with a good solubility in the respective solvent (for example an active ingredient belonging to the group of Beta-2-Sympathomimetica).

Generally, the nebulizer 1 operates with a pressure of 5 to 250 MPa, for the nebulization of aqueous fluids preferably 10 to 50 MPa, wherein pressure peaks of up to 100 MPa (1000 bar) (typically about twice the size of the normal operation pressure) can occur during priming of the nebulizer, i.e. when fluid 2 is distributed in the nebulizer 1 (i.e. in the pressure chamber, nozzle channels etc.) for the first time at the first actuations of the fluid pump 5.

For the nebulization of non-newtonian fluids 2 an operation at a comparatively high pressure range is preferable: Preferably the nebulizer 1 operates with a pressure of 10 to 100 MPa. most preferably 20 to 50 MPa on the fluid 2. Preferably, the energy for the pressure generation is supplied by a drive spring 7 with a mean force ranging from 30N to 120N, most preferably with a mean force ranging from 45 N to 90N, for instance 60N. (The use of an 120N spring would result in pressures up to 1000 bar but requires a rather high handling force for the tensioning of the device)

Preferably, a volume of fluid 2 delivered per stroke of 10 to 50 μl, preferably 10 to 30 μl, most preferably about 15 μl.

The fluid 2 is converted into or nebulized as aerosol 14, the droplets of which have an aerodynamic diameter of up to 20 microns, preferably 3 to 10 microns (with a high fraction of particles being smaller 5 microns for inhalation in case of the nebulizer 1 being an inhaler). Preferably, the generated jet spray has an angle of 20° to 160°, preferably 80° to 100°. These values also apply to the nebulizer 1 according to the teaching of the present invention as particularly preferred values.

A user or patient (not shown) can inhale the aerosol 14, preferably while air can be sucked into the mouthpiece 13 through at least one optional air supply opening 15.

The droplet size of the aerosol generated by impinging jet atomization depends on the diameter of the nozzle channels 12*d*, from where the jets emerge, the velocity of the jets and surface tension (example: for water 0.072 N/m) and density of the fluid 2. The velocity of the jets depends on the channel dimensions and the pressure exerted on the fluid 2. (For instance: The pressure generated by a fluid pump 5 with a spring force of 45 N pressing on a piston (preferably formed by conveying tube 9) with 1.5 mm diameter is of the order of 25 Mpa (=250 bar), which might be reduced by 20%, to a value of around 20 MPa when the fluid 2 reaches the nozzle channels 12*d*.)

When the fluid 2 flows in a channel, the resulting flow has flow profile with the flow velocity being zero on the surfaces of the channel and a maximum velocity in the middle of the channel. Thus shear forces occur when the fluid 2 travels through the nozzle channels 12*d*. The shear rate is defined as the measure of the extent or rate of relative motion between adjacent layers of a moving fluid, i.e. the shear rate is the velocity gradient in relation to the distance from the channel surface.

Eventually, a boundary layer will develop from the surfaces of the channel and the flow profile is further determined by a rather flat profile in the center and a sharp decrease of the flow velocity at the channel surfaces.

According to the invention, the velocity gradients/shear forces occurring in the nozzle channels 12*d* are used for reducing the viscosity of a non-newtonian fluid or non-newtonian liquid. Preferably, the reducing of the viscosity (in particular down to viscosities below 1.6 centipoise) occurs already upon the start of the dispensing of the fluid 2 through the nozzle 12, because then the fluid can actually be sprayed continuously/for the remaining duration of the generated puff.

The reduction of the viscosity can be explained according to the following theory: When pressure is initially applied to the fluid 2, the fluid has its initial high viscosity η. Assuming a simple viscous flow as a first reaction to the applied pressure, the flow initially behaves according to the law of Hagen-Poiseuille when starting the dispensation through the nozzle channels 12*d*. Such a flow has a parabolic flow profile and the highest velocity gradient occurs at the channel surface. Thus the velocity gradient can be high enough for reducing the viscosity in such a way that the center velocity can increase quickly to a level suitable for generating the jets required for the double-jet-impinging principle.

For calculations according to this model, the (according to the embodiment of FIG. 3 rectangular) nozzle channel 12*d* is substituted by round tubes with a hydraulic diameter $d_h$=2 d b/(d+b) (d being the height and b being the width of the channel, exemplary values for calculation being d=5.6 μm=5.6*10*$^{-6}$ m and b=8 μm=8*10*$^{-6}$ m). The flow presses with a force k onto the inner surface of the tube/nozzle channel (with the tubes inner surface being F=πl$d_H$/2=πrl, with a tube length l, for instance l=40 μm):

$$k = \eta F\frac{dv}{dr} = \pi r^2\frac{dp}{dl}$$

From this the velocity gradient can be derived to be $$\frac{dv}{dr} = \frac{r\Delta p}{\eta l}$$

with a pressure difference Δp (for instance 20 MPa as a normal operational pressure) along the total tube length l.

The mean velocity in the tube is given by the ratio of volume flow V/t and cross section, i.e.

$$\bar{v} = \frac{V}{t\pi r^2} = \frac{r^2\Delta p}{8\eta l}$$

Generally, when the velocity gradient at the surface becomes high enough for a suitable reduction of the viscosity of the non-newtonian fluid, the velocity of the flow/jet increases and the increased velocity can be maintained.

For a fluid with a viscosity of 100 cP=0.1 kg/(m s) (for instance a suspension) this model gives a velocity gradient of 16*10$^6$/s for the mentioned exemplary values (which is regarded as a medium viscosity here; for comparison: the (low) viscosity of water would result in a gradient of $1.6*10^9$/s in this context—the shear rates in this type of device are very high indeed). In order to achieve the velocity increase necessary for spraying, the shear-dependence of the viscosity must be of such a form that it significantly decreases when such a velocity gradient is applied.

The same calculation for an emulsion with an initial viscosity of $10^4$ cP=10 kg/(m s) results in a velocity gradient of $1.6*10^5$/s. Like in the suspension example, this velocity gradient has to be sufficient for the here required viscosity reduction. This magnitude of shear rates occurring at the nozzle of the here discussed nebulizer should be sufficient for effecting a decrease in viscosity for those fluids for which a shear rate dependency of the viscosity is known. (Even if the calculations shown here are based on idealized assumptions for the processes occurring in the nebulizer) Often cited examples for such a shear rate dependency start out with viscosities between 100 and $10^7$ cP and the shear rate typically starts effecting the viscosity at shear rates of 10/s and below (a nice example for a strong shear rate dependency is 0.05% polyacrylamide solution which starts out at about $2*10^6$ cP viscosity with a linear shear rate dependency starting at $10^2$/s).

It has to be noted that the calculation above is based on the normal operation pressure of the nebulizer. Preferably, an enhanced pressure pulse occurring when the nebulizer is filled with fluid for the first time is used for initiating the share rate, i.e. the pressure peak occurring when priming the nebulizer for the first time. As this pressure pulse coincides with the build-up of the shear rate needed for achieving the required viscosity reduction in case of a non-newtonian fluid, the suitability of the system for nebulizing the non-newtonian fluid is enhanced.

In particular, the pressure pulse for a nebulizer of the here discussed dimensions has a magnitude of 30 MPa-65 MPa (or up to 200 MPa for very strong springs). For the above mentioned calculated example of an emulsion with a viscosity of 100 cP this means that that enhanced start-up velocity gradient according to the here presented calculation can be as high as $54*10^6$/s ($1.6*10^8$/s).

When the initial viscosity increases, the velocity gradient according to this model decreases (plus: the boundary layer thickness also increases with the viscosity). Thus a very high viscosity would prevent the formation of a high shear rate, i.e. highly viscous fluids must have a strong shear-dependence of the viscosity already at low share rates for enabling the nebulization with such a system. However as the above shear rate calculations show, with shear rates as high as for this pump-nozzle-set-up anything which eventually gets to flow to the nozzle channels will be sheared.

Data-example for the nebulization of structured fluids with a soft-mist inhaler/nebulizer according to FIG. 1:

1. Spraying of a "7% Budesonide"-Nanosuspension:

An aqueous nanosuspension of Budesonide (71,079 mg/mL) was prepared in 1% HPC-SL (dispersion aid) inclusive 0.0075% Tween 80 and 0.0075% SDS (both tensides; Tween80=Polysorbat 80 is an o/w emulsifier, SDS=sodiumlaurylsulfate is a=/W emulsifier). HPC-SL (hydroxypropylcellulose) is used for stabilizing the nanosuspension, i.e. a dispersing aid, and its' addition induces an increase in viscosity of the resulting fluid. For the viscosity of this nanosuspension a value of 106 cP was measured (start value in regard to a share rate dependency) (laboratory conditions, i.e. at room temperature). A milling process has been used for size reduction of the budesonide particles.

A diagram of a typical Zetasizer-measurement of the suspensions' solid particles (after nebulization) shows a stable monomodal distribution of particle sizes peaking radius size of about 132 nm and a peak width of 46 nm (The particles showed a similar size distribution prior to nebulization, as well).

Experiments with the "7%" suspension of Budesonide in water have shown that the suspension can be nebulized with a nebulizer 1/a softmist inhaler according to FIG. 1-4 reproducibly (test set-up: spring force 45N, nozzle channels with a width of 8 μm and a of height 5.6 μm): In-use testing (in average daily actuation with two actuations) showed the tested nebulizers to dispend a constant volume of the suspension for the three months during which the experiment was conducted. The initial filling of the nebulizer was possible without additional pressurization of the fluid during withdrawal of the fluid from the container (the option of additional pressurization is in particular preferable for the nebulization of more highly viscous fluids and is discussed later on)—most of the tested systems even showed some sort of aerosol generation upon the first actuation; for all nebulizers tested with the 7% Budesonide nanosuspension the priming was acceptable (for the ejection of a full dose usually several actuations are needed for this kind of system even when nebulizing aqueous liquids).

Surprisingly the fine particle fraction of the nebulized suspension is even higher than for a classical aqueous solution nebulized with a similar nebulizer (nebulizing occurring according to the double-jet-impinging principle): data Measurements with a cascade impactor (type next generation impactor. NGI for short) showed a fine particle fraction (fraction of aerosol particles with diameters of 5 microns and less) in the range of 60%. Even higher fine particle fraction seem to be achievable depending on the kind and concentration of nanoparticles and/or the additives present in the suspension.

A possible explanation for this is that once the jets generating the spray obtain the required flow velocity for forming a liquid sheet, the surface tension of the fluid is a relevant parameter regarding the formation of aerosol droplets leaving the sheet. Probably, the surface tension for a nanosuspension is reduced (compared to the surface tension of the classical aqueous solution (medical formulation)), i.e. the fluid surface breaks up more easily where the solid particles are present.

2. Spraying of a Oil-In-Water Emulsion:

A commercially available emulsion comprising 0.1% cyclosporine in water (Ikervis®—eye drops for treatment of severe keratitis, comprising water, cyclosporine, Glycerol, Cetalkoniumchlorid, medium-chain triglycerides (MCT), Natriumhydroxid, Poloxamer 188 and Tyloxapol) has been successfully nebulized with a softmist inhaler according to FIG. 1-4 (test set-up: spring force 60N, nozzle channels with a width of 8 μm and a of height 5.6 μm): Surprisingly the fine particle fraction of the nebulized suspension is even higher than for a classical aqueous solution nebulized with a similar nebulizer (nebulizing occurring according to the double-jet-impinging principle): data Measurements according to a laser-diffraction technique showed a fine particle fraction (fraction of aerosol particles with diameters of 5 microns and less) in the range of 75% and a spray time of 1.6 s. (For ophthalmologic applications spring force and nozzle diameters should be redimensioned to obtain only a small inhalable fraction—the measurement with this set-up was only for proofing the ability of the system for generating a spray with an oil-in-water emulsion).

Shear rate depend measurements of the viscosity revealed a start viscosity (i.e. a viscosity "at rest", room temperature) of 87.7 centipoise which was quickly reduced down to 1 centipoise already at a shear rate of 4 $s^{-1}$, i.e. already a small applied pressure successfully reduces the viscosity of the formulation down to the viscosity of water (measured with a concentric cylinder viscosimeter of the so called "searle type", i.e. comprising a rotating inner cylinder). The initial filling of the nebulizer was possible without additional pressurization of the fluid during withdrawal of the fluid from the container, i.e. the underpressure created in the pressure chamber 11 during the first cocking or first tensioning process, when the conveying tube 9 (which is also forming a pressuring ram in the pressure chamber 11) is partly moved out of the pressure chamber 11, is sufficient for the withdrawal of this fluid 2 (i.e. this emulsion) out of the container 3 into the fluid pump 5 or its pressure chamber 11: The tested systems showed some sort of aerosol generation upon the first actuation, i.e. the priming of the system with this emulsion is good/can be completed within only a few actuations.

3. Spraying of Gels

Gels Containing Gelling Agents in an Aqueous Continuous Phase

A gel containing 0.5% amylopectine (derived from corn starch) as a gelling agent in an aqueous continuous phase has been prepared by disperging 0.5 g starch in 100 ml cold water and heating it to 60-70° ° C. while stirring. The gel has been successfully nebulized with a nebulizer 1/softmist inhaler according to FIG. 1-4 (test set-up: spring force 45N, nozzle channels with a width of 8 μm and a of height 5.6 μm): data Measurements according to a laser-diffraction technique showed a fine particle fraction (fraction of aerosol particles with diameters of 5 microns and less) in the range of 70% and a spray time of 1.25 s.

Even a similarly prepared gel containing 1.7% amylopectine as a gelling agent in an aqueous continuous phase has been successfully nebulized with a nebulizer 1 according to FIG. 1-4 (test set-up: spring force 45N, nozzle channels with a width of 8 μm and a of height 5.6 μm), although the increase of the gelling agent's concentration resulted in a reduced fine particle fraction and longer spray times: data Measurements according to a laser-diffraction technique showed a fine particle fraction in the range of 45% and a spray time of 1.4 s.

A gel containing 0.3% HEC (hydroxyethylcellulose) as a gelling agent in an aqueous continuous phase has also been successfully nebulized with a nebulizer 1/softmist inhaler according to FIG. 1-4 (test set-up: spring force 45N, nozzle channels with a width of 8 μm and a of height 5.6 μm): data Measurements according to a laser-diffraction technique showed a fine particle fraction (fraction of aerosol particles with diameters of 5 microns and less) in the range of 50% and a spray time of 1.5 s. When increasing the concentration of the gelling agent to 0.6% HEC, the nebulization of the gel was still possible with a nebulizer 1 of the same set-up, but the fine particle fraction has decreased to about 30% and the spray time has increased to 1.9 s. When increasing the HEC-concentration to 1.0% the gel has not been sprayable anymore.

For both gelling agents, the viscosity of the gel increased with increasing the concentration of the gelling agent. The initial filling of the nebulizer 1 was nevertheless still possible without additional pressurization of the fluid during withdrawal of the fluid from the container, although the nebulizer 1 had to be handled with care during priming: The first tensioning or cocking had to be conducted comparatively slowly (i.e. for the nebulizer 1 the inner part 17 was only slowly rotated relative to the housing part 16 (180° rotation) for transferring the nebulizer 1 from the non-tensioned state as depicted in FIG. 1 into the tensioned state as depicted in FIG. 2).

In particular for high concentrations of the gelling agent, the use of a nebulizer 1 with additional pressurization of the fluid during withdrawal of the fluid from the container (see later discussion regarding embodiment according to FIG. 6-9) is preferable: In an additional experiment a gel containing 8.5% amylopectine in an aqueous continuous phase was prepared by sprinkling 2.5 g amylopectine into 29.5 g cold water and bringing it to (shortly) boil while stirring. Shear rate depend measurements of the viscosity revealed a start viscosity (i.e. a viscosity "at rest") of 17000 centipoise which was reduced down to 100 centipoise at a shear rate of 2000 $s^{-1}$. When dispensing this viscous gel with a nebulizer 1/softmist inhaler according to FIG. 1 with a cartridge according to FIG. 4, a significant number of nebulizer actuations (i.e. a number of tensioning steps) had to be done before the amount of dispensed gel increased to a reproducible value level (i.e. when the pump was sufficiently filled for the pump mechanism to work more reproducible) (for the first four actuations no or only little amounts of gel were dispensed by the nebulizer). In comparison, when dispensing this viscous gel with a similar nebulizer 1/softmist inhaler with additional pressurization during fluid withdrawal (here a nebulizer according to FIG. 9 with a cartridge according to FIG. 6), surprisingly an amount exceeding 90% of the reproducible value level (mainly determined by the dimensioning of the pump mechanism) could be dispensed upon the first actuation of the nebulizer 1 (wherein the very same nebulizer was tested with both cartridges, but cleaned and emptied in between).

Medical Gel Formulation

A commercially available gel for ophthalmologic treatment ("Artelac Nighttime Gel®"—an eye gel designed for people with dry eyes (chronic tear dysfunction) wherein all three layers of the tear film are complemented, the gel containing 2 mg Carbomer, triglyceride lipids and sterile water, plus Sorbitol und Natriumhydroxid and Cetrimid as preservative) has been successfully nebulized with a nebulizer 1/softmist inhaler according to FIG. 1-4 (test set-up: spring force 45N, nozzle channels with a width of 8 μm and a of height 5.6 μm): data Measurements according to a laser-diffraction technique showed a fine particle fraction in the range of 43% and a spray time of 1.8 s. Shear rate depend measurements of the viscosity revealed a start viscosity (i.e. a viscosity "at rest" at room temperature) of 300.000 centipoise which was linearly reduced down to 200 centipoise at a shear rate of 1000 $s^{-1}$—no higher shear rates could be applied with the used testing equipment (a concentric cylinder viscosimeter of the so called "scarle type", i.e. comprising a rotating inner cylinder), but due to the successful nebulization it has to be assumed that the viscosity is even further reduced due to the higher shear rates in the nozzle channels 12*d*.

The gel was very viscous so that additional pressure/force was needed for the initial filling of the nebulizer 1. In this experiment the additional force used was a combination of gravity and shock impulse: The nebulizer 1 was positioned upside down i.e. with gravity pulling the fluid 2, i.e. the gel, into the conveying tube 9, the flow being initiated by knocking on the system.

When repeating the priming procedure with a similar nebulizer 1 comprising a stronger spring (spring force 90N instead of 45N), the initial filling could be done more steadily but nevertheless several actuations (6) were needed in which the mass of the dispensed dose slowly rose up to a reproducible value level characteristic for this nebulizer.

4. Spraying of Liposomal Fluids

Various liposomal fluids were prepared by solving soy lecithin in ethanol, adding PEG 400 (polyethylene glycol) and stirring (dispersed in water). Afterwards a separately stirred mix of glycerine and water (high-purity) is added followed by further stirring. For variations the amounts of soy lecithin (0,625% m/m to 25% m/m respectively 75 mg-3000 mg), of glycerine (0-16.7 vol % respectively 0-2 ml) and of PEG (0-8.3 vol % respectively 0-1 ml) were varied in a constant amount of water and ethanol (6 ml and 3 ml). In further variations of the fluids, part of the soy lecithin was exchanged by cholesterol for the stability of the fluid (0-35 mol % cholesterol to go with 100-65 mol % lecithin, preferably the cholesterol content was 25 mol %, i.e. for example in a socalled “1.25% m/m lecithine formulation” 22.52 mg cholesterol went with 112 mg soy lecithine in 3 ml ethanol and 6 ml water with possible additions of PEG 400 and glycerol).

The average size of the particles and the polydispersion index (PDI) was determined by Zetasizer-measurements of the various liposomal fluids before and after nebulization with a nebulizer 1/a softmist inhaler according to FIG. 1-4 (test set-up for lecithin concentrations up to and including 10%: spring force 45N, nozzle channels with a width of 8 μm and a of height 5.6 μm; spring force 90N for nebulizing a formulation with 25% lecithin). All tested liposomal fluids could be nebulized by a nebulizer 1/softmist inhaler according to FIG. 1-4, although for a comparatively high lecithin content (i.e. for a viscous fluid with a viscosity of 680 centipoise) a comparatively high spring force and/or more priming effort was required for successful nebulizing the fluid—but even then according to laser-diffraction measurements a fine particle fraction in the range of 50% could be reached for a fluid containing 25% lecithin.

For fluids not containing cholesterol or other contents for enhancing the stability of the liposomes/lipid particles, all measurements were conducted within a day of preparing the fluids as Zetasizer-measurements indicated the formation of agglomerates within a time span of just four days in the fluid: The measured values both for average particle size and for the PDI had almost doubled for a 1.25% m/m lecithine formulation (150 mg soy lecithine in 1 ml PEG 400, 2 ml glycerine, 3 ml ethanol and 6 ml). However, measurements of the 4 day old fluid after nebulization with the nebulizer 1 revealed similar values as for a similarly prepared fresh fluid, indicating that the nebulization process in the nebulizer 1 breaks up agglomerates which form during storage.

Zetasizer measurements for several of the various liposomal showed PDI-values above 70%, i.e. values indicating a significant polydispersity of the fluid. In particular fluids containing a comparatively high amount of glycerine (16.7 vol %) mostly showed PDI-values above 70% (both for measurements of the fluid as such and of the nebulized fluid), especially when also containing PEG 400 (measured for “1.25% m/m lecithine formulations”). For the same fluids, data Measurements according to a laser-diffraction technique showed an increased fine particle fraction for fluids with decreased contents of PEG 400 and glycerine; for the tested “1.25% m/m lecithine formulations”, the highest fine particle fraction values (about 65% for the fraction of aerosol particles with diameters of 5 microns and less) were obtained for a fluid not containing any PEG 400 and glycerine (the reduction of glycerine having an even stronger effect on the fine particle fraction of the nebulized fluid than the reduction of PEG). I.e. also for liposomal fluids, the fluid to be nebulized with the system according to the invention should contain less than 15% glycerin (although a test fluid comprising a concentration of about 17% glycerin could be nebulized, too, as described above), in particular less than 10% glycerin or most preferably less than 1% or no glycerin.

For fluids with a comparatively high contents of PEG 400 (8.3 vol %) and glycerine (16.7 vol %), even comparatively changes of the soy lecithine content showed a strong impact on the values obtained by Zetasizer measurements: PDI=32% for 0.83% m/m lecithine (both before and after nebulization), PDI=53% (85% after nebulization) for 1.25% m/m lecithine and PDI=78% (100% after nebulization) for 1.67% m/m lecithine (the overall data show an increase in the PDI-values when fluids with a high PEG 400 content (here 8.3 vol %) are nebulized).

Laser-diffraction measurements of nebulized fluids not containing any PEG 400 and glycerine showed a dependency of the fine particle fraction values (fraction of aerosol particles with diameters of 5 microns and less) of the soy lecithine concentration: The fine particle fraction decreases when the lecithine concentration is increased, but the effect is not significant for lecithine concentrations of up to 5% m/m; fine particle fraction values of up to 70% and more could be reached for lecithine concentrations up to 5% m/m and for a lecithine concentration of 10% m/m a fine particle fraction of 50% was obtained. Parallely, corresponding spray durations (likewise obtained by laser-diffraction measurements) lengthened from 1.45 s to 1.71 s for an increase of the lecithine concentration from 0.625% to 10% m/m. This corresponds to an increase of the fluid’s viscosity at rest for increasing lecithine concentrations: A viscosity of about 1.7 cP+/−0.6 cP centipoise was determined for a fluid with a lecithine concentration of 0.625% m/m (no PEG, no glycerine), a viscosity at rest of 286 centipoise for a lecithine concentration of 10% m/m and a viscosity of 681 centipoise for a lecithine concentration of 25% m/m. (please note that as the viscosity data for the lecithine concentration of 0.625% m/m indicated no dependency on the shear rate, but merely an arbitrary data fluctuation, in this case not the first value (1.24 cP) of the data set taken for increasing shear rates was taken as the value for the viscosity “at rest”, but an average of the values obtained for shear rates between 0.1/s and 1/s)

Figure 11:
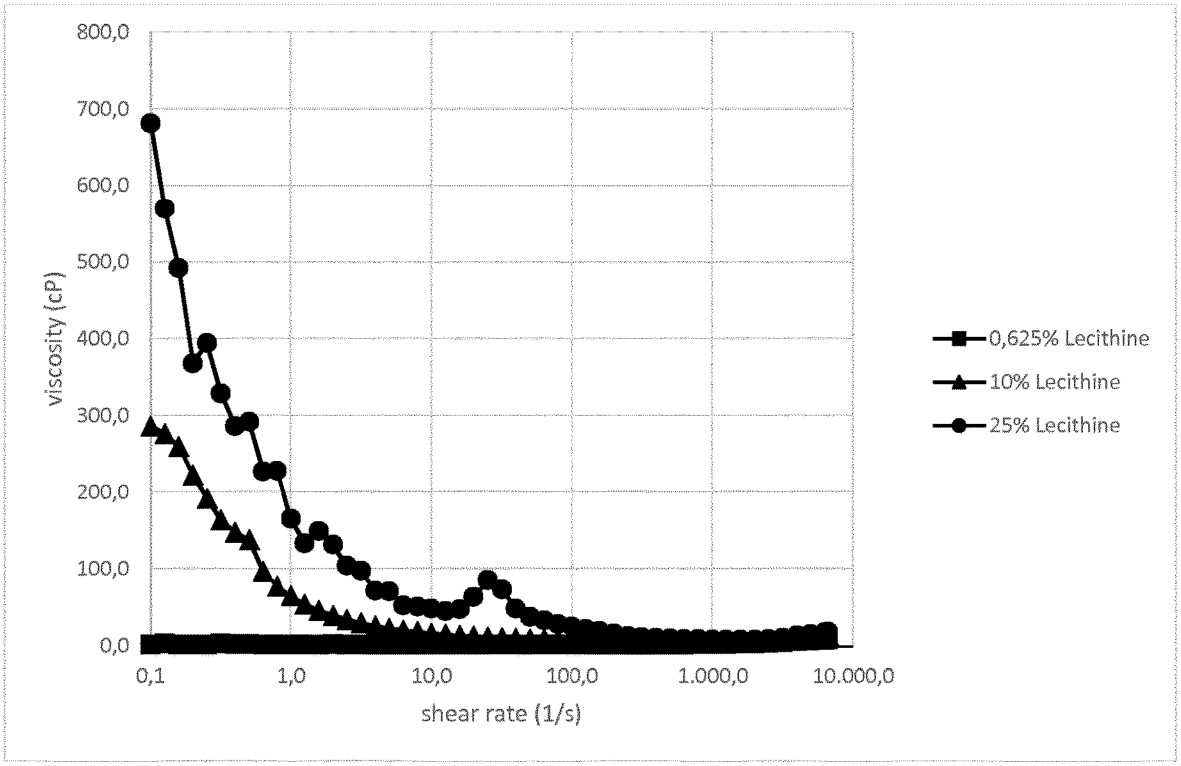
FIG. 11 a diagram of the viscosity of liposomal fluids with different lecithine concentrations as a function of the shear rate.

The measurements of the viscosity revealed a non-newtonian behavior for the liposomal fluids, in particular a shear rate dependence of the fluid’s viscosity. The diagram in FIG. 11 shows the shear rate dependency of fluids with different lecithine concentrations. The viscosity for the fluid with a lecithine concentration of 0.625% m/m did not show a significant shear rate dependency and mostly remained below 2 centipoise until (as for all measurements at very high shear rates) the ethanol in the fluid started to evaporate significantly. The tested liposomal fluids with higher viscosities at rest however showed shear rate dependent viscosity values with values dropping down below 10 centipoise at a shear rate of 50 $s^{-1}$ for the tested fluid with a 10% m/m lecithine concentration and at a shear rate of 500 $s^{-1}$ for the tested fluid with a 25% m/m lecithine concentration.

For nebulizing the comparatively viscous fluid with the 25% lecithine concentration (viscosity of 680 centipoise at rest at room temperature), the nebulizer 1/softmist inhaler according to FIG. 1 with a cartridge according to FIG. 4 was equipped with a stronger spring than for nebulizing for instance the fluid with 10% m/m lecithine concentration (90N spring force instead of 45N). Even with the stronger spring, a significant number of nebulizer actuations (i.e. a number of tensioning steps) had to be done before the amount of pumped up fluid mass increased to a reproducible value level (i.e. when the pump was sufficiently filled for the pump mechanism to work more reproducible) (five actuations/operations of the nebulizer 1 were needed to pump out a mass with an amount exceeding 75% of the reproducible value level for this fluid). In comparison, when dispensing this viscous liposomal fluid with a nebulizer 1 with additional pressurization during fluid withdrawal (using a set-up for nebulizer 1 according to FIG. 9 with a cartridge according to FIG. 6), surprisingly a mass with an amount exceeding 75% of the reproducible value level (mainly determined by the dimensioning of the pump mechanism) could be dispensed upon the first operation of the nebulizer 1.

Figure 9:
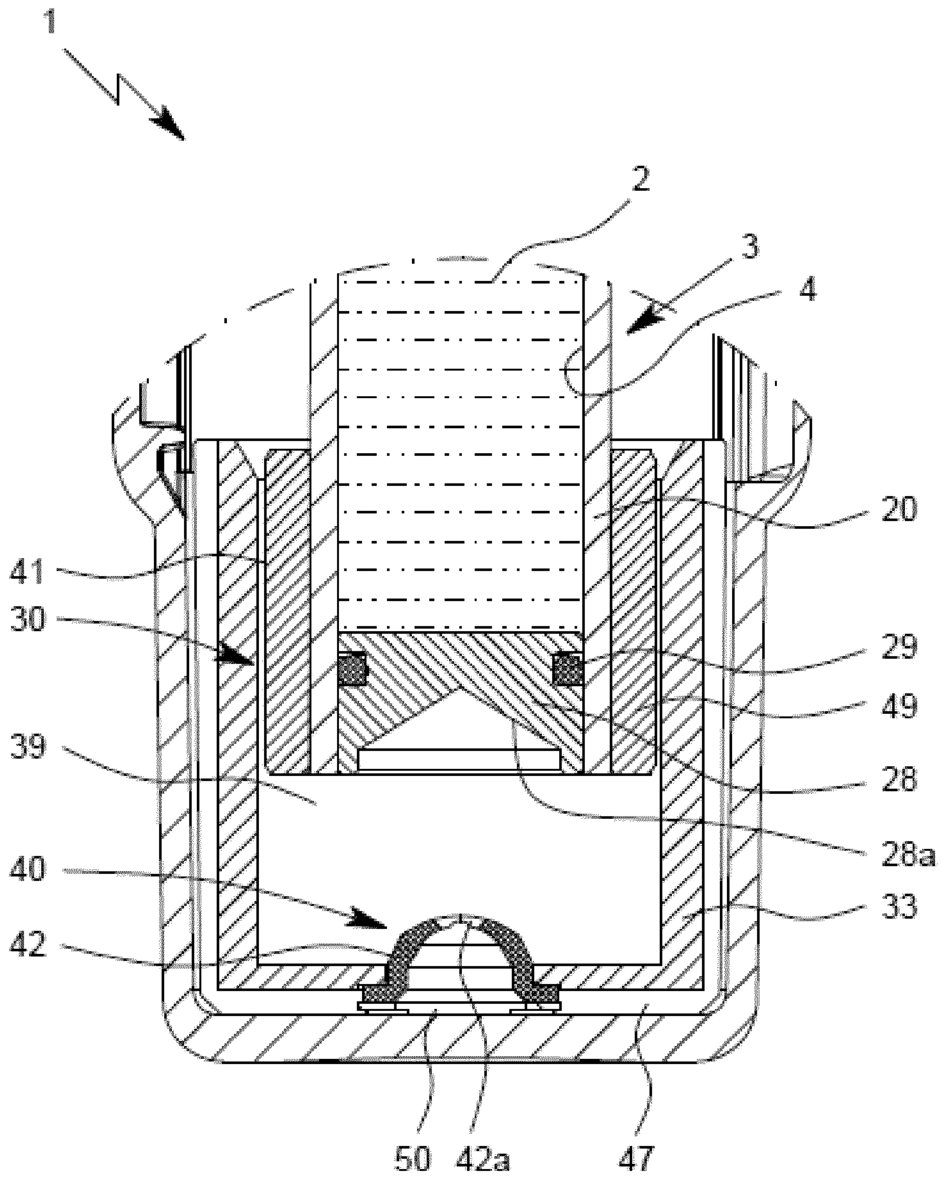
FIG. 9 a schematic section of a lower part of the nebulizer in the non-tensioned state similar to FIG. 7, but with a modified valve.
Figure 12:
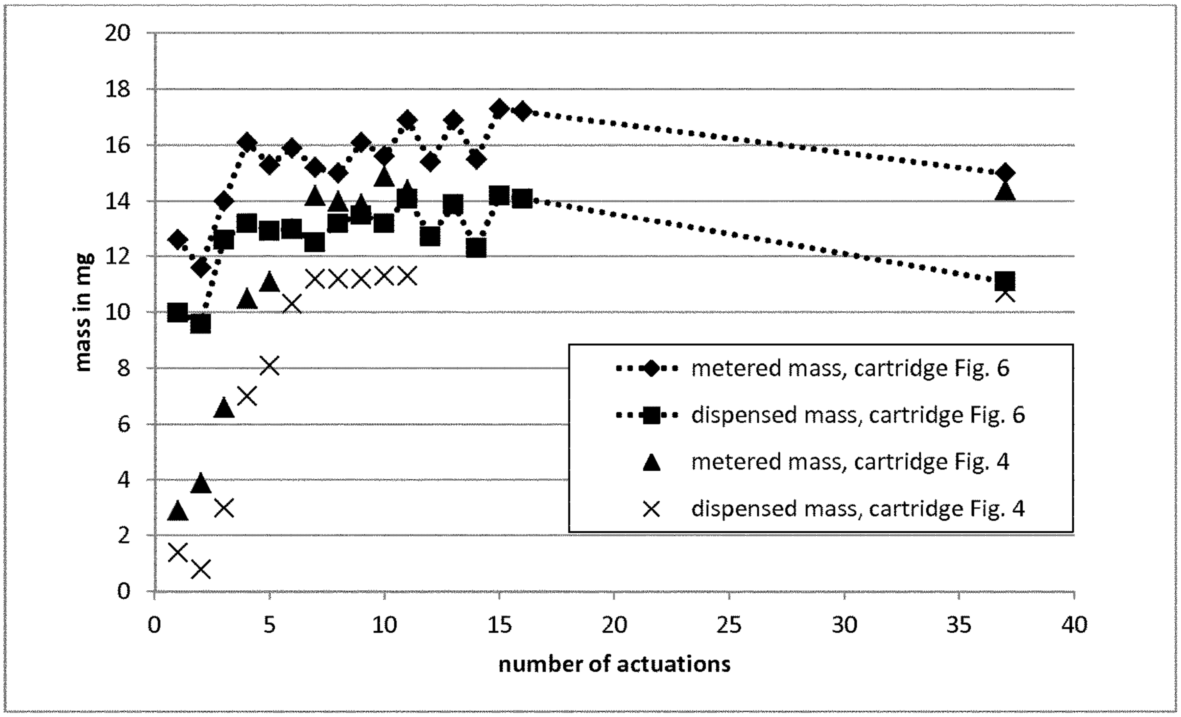
FIG. 12 a diagram of the mass dispensed from different embodiments of the nebulizer 1 for a liposomal fluid with 25% lecithine concentrations as a function of the number of actuations.

The diagram of FIG. 12 shows how the mass which is pumped up from the nebulizer 1 ("metered" mass)/the mass dispensed as spray from the nebulizer 1 changes with the number of actuations/operations of the nebulizer 1 after a cartridge with the fluid containing 25% m/m lecithine is inserted in the nebulizer 1/fluidically connected to the nebulizer 1 (i.e. connected to the conveying tube 9). For this experiment the very same nebulizer 1 was tested with two different types of cartridges, i.e. after the nebulizer 1 was tested with a cartridge (without additional pressurization) according to FIG. 4, it was cleaned out and emptied and a cartridge according to the design shown in FIG. 6 was attached (wherein the housing part 18 was adapted/exchanged to suit the new cartridge, i.e. to form a system as shown in FIG. 9).

During the first actuations the pump mechanism of the nebulizer 1 has to be filled first, before fluid 2 can exit the nozzle 12 of the nebulizer 1, i.e. before any fluid mass can be pumped out of the nebulizer 1. Therefore, it is typical for this kind of nebulizer that some priming actuations (successive steps of actuation and operation) are required until the mass pumped out of the nebulizer reaches a reproducible value level. When discussing the mass of the fluid 2, there are two different kind of mass which can be considered: the mass of the actually generated spray (called "dispensed mass" here) or the mass pumped out at the nozzle 12 (called "metered mass" here) upon operation of the nebulizer 1 (or upon pressing the button 8*b* as in the shown embodiment) which also contains droplets forming at the surface of the nozzle 12 during spray formation. Naturally, both kind of mass-values show the same priming dependency and only differ according to the individual droplet formation in each actuation. In FIG. 12 can be seen that the number of actuations/operations required for priming the nebulizer, i.e. for bringing the dispensed mass/metered mass to a steady value level is smaller when the cartridge with additional pressurization (set-up according to FIGS. 6 and 9) is used in comparison to when a cartridge without additional pressurization is used: The initial filling of the pump mechanism of the nebulizer 1 is helped along by the additional pressurization (without the additional pressurization the sucking force of the pump is not completely sufficient to enforce the flow of the tested viscous fluid).

Surprisingly, the data shown in the diagram of FIG. 12 show that the steady/reproducible value levels both for metered mass and dispensed mass are higher when the nebulizer 1 is used with a cartridge with additional pressurization. A possible explanation for this is that, even after the state of a steady mass ejection has been reached, the filing of the nebulizer pump with the (viscous) fluid is not fully complete when no additional pressurization is used. Internally captured air bubbles or dead volumes might decrease the steady value level of the metered mass/dispensed mass.

According to a not-shown alternative, the nebulizer 1 is constructed as a portable nebulizer for applying fluids on the cornea or on the ocular connective tissue, i.e. as a nebulizer for ophthalmological applications. Such a nebulizer 1 for ophthalmological applications comprises an eye-piece instead of mouthpiece 13 or comprises an adapter as disclosed in WO 03/002045 A1. the adapter being fixed to the mouthpiece 13. On the eye-side the eye-piece or the adapter is constructed so that it can fit round an eye. The force of spring 7 and the channel nozzles 12*d* are preferably dimensioned in such a way that the spray produced with the device consists of aerosol particles/droplets of a diameter of at least 10 microns, preferably of about 20 microns or more (the inhalable fraction of aerosol particles is preferably very low for an ophthalmologic nebulizer so that any side effects due to inadvertently inhaling the particles are reduced). The above described experiments with Ikervis® and Artelac Nighttime Gel® simply proofed the sprayability of these ophthalmologic formulations with a nebulizer 1 according to the invention, however by chance the experiment was conducted with an inhaler, i.e. the force of spring 7 and the nozzle dimensions had not been chosen for generating aerosol particles of diameters suitable for the application on the eye. However, this is a matter of experts choosing a suitable design according to the laws governing the formation of the droplets.

For better understanding of later described embodiments, some further technical details of the embodiment of the nebulizer according to FIG. 1-2 will be explained now:

The nebulizer 1 comprises preferably a housing 1*b* and/or (upper) housing part 16 and optionally a biasing or inner part 17 preferably which is rotatable relative thereto (FIG. 2) and/or has an upper part 17*a* and a lower part 17*b* (FIG. 1).

The nebulizer 1 or housing 1*b* comprises preferably a (lower) housing part 18. This part 18 is in particular manually operable, and/or releasable fixed, particularly fitted or held onto the inner part 17, preferably by means of a retaining element 19.

Preferably, the housing parts 16 and 18 and/or other parts form the housing 1*b* of the nebulizer 1.

In order to insert and/or replace the container 3, preferably the housing 1*b* can be opened and/or the housing part 18 can be detached from the nebulizer 1, inner part 17 or housing 1*b*. The housing part 18 preferably forms a cap-like lower housing part and/or fits around or over or covers a lower free end portion of the (inserted) container 3.

Generally and preferably, the container 3 can be inserted before the housing 1*b* is closed and/or before the housing part 18 is connected to the housing 1*b*. The container 3 may be inserted, opened and/or fluidically connected to the delivery mechanism or fluid pump 5 automatically or simultaneously when (completely) connecting the housing part 18 to the housing 1*b*/nebulizer 1 and/or when (completely) closing the housing 1*b*/nebulizer 1. Preferably, the container 3 is open or fluidically connected when tensioning the nebulizer 1 for the first time with the current container 3.

Preferably, the nebulizer 1 or drive spring 7 can be manually activated or tensioned or loaded, in particular by actuation or rotation of an actuation member, here preferably by rotating housing part 18 or any other component.

The actuation member, preferably the housing part 18, can be actuated, here rotated relative to the upper housing part 16, carrying with it or driving the inner part 17. The inner part 17 acts on a gear or transmission to transform the rotation in an axial movement. As a result the drive spring 7 is tensioned in the axial direction by means of the gear or transmission (not shown) formed between the inner part 17, in particular its upper part 17*a*, and the holder 6 and acting on the holder 6. During tensioning the container 3 and holder 6 are moved axially downwards until the container 3 assumes an end position as shown in FIG. 2. In this activated or tensioned state the drive spring 7 is under tension and can be caught or held by the blocking element 8. During the nebulizing process the container 3 is moved back into its original position (non-tensioned position or state shown in FIG. 1) by (the force of) the drive spring 7. Thus, the container 3 executes a lifting or stroke movement during the tensioning process and during the nebulizing process.

As the drive spring 7 is tensioned the container 3 moves with its end portion or base 22 (further) into the housing part 18 or towards the end face thereof. Thus temporary interactions between container 3 or its base 22 with the housing part 18 or any device/mechanism assembled therein can be provided.

The nebulizer 1 comprises preferably an indicator device 125, which counts in particular actuations of the nebulizer 1, preferably by detecting its' tensioning or the rotation of the inner part 17 relative to the upper part 16 or housing 24. Preferably, the counter device 25 or an associated locking device 26 locks the nebulizer 1 against (further) actuation or use, e.g. blocks further rotation of the housing part 18/inner part 17 and, thus, tensioning of the nebulizer 1 or its drive spring 7 and/or blocks actuation of the blocking element 8, in a locked state when a certain number of actuations or operations or discharged doses has been reached or exceeded. For instance, this number of actuations can be preset according to the number of doses which can reliably be extracted from the container and/or which (in dependence of the particle load of the fluid) can reliably pass the filter stages without blocking a filter stage significantly.

Details of a suitable locking device are disclosed in WO2004/024340 A1.

The container 3 is preferably of rigid construction, the fluid 2 in particular being held in a variable or collapsible volume 4, such as a flexible or compressible inner container of variable volume in the container 3. Such a container 3 could be constructed as described in WO 2009/115200 A1 which discloses an embodiment of a container storing an in particular ethanol-based liquid in a collapsible bag.

FIG. 4 shows an embodiment of a container which had initially been developed for storing aqueous formulations and wherein the inner container is a collapsible bag.

In particular, the container 3 comprises a rigid casing 20, a fluid outlet or head 21 and/or a base 22 opposite the outlet/head 21 as shown in FIG. 4. Preferably, the container 3, casing 20 or base 22 is provided with a venting opening or hole 23 which is opened before or during first use.

In the embodiment according to FIG. 1 and FIG. 2, an aeration device 18*a*, such as an axially acting spring with a piercing element 18*b* or a device comprising a preferably hollow needle with a tapered and/or inclined and/or sharp tip, is arranged in the housing part 18 and comes in contact with the base 22 of the container 3 when the container moves into the housing part 18. When the base 22 of the container 3 makes contact with it for the first time, the aeration device 18*a*, opens or pierces the container 3 or a seal or foil 26 thereon, to allow air in or aeration, preferably by opening or piercing venting hole 23. The venting hole 23 allows for pressure compensation inside the container 3 when fluid 2 is drawn from the container 3 during the tensioning of the nebulizer 1.

In particular, the container 3 as shown in FIG. 4 comprises in addition to the outer, preferably metallic casing 20 an inner, preferably rigid container or shell 24. The shell 24 encompasses or surrounds the bag/variable volume 4.

The shell 24 is preferably made of plastics and/or extends up to the outlet or head 21.

Preferably, the shell 24 is rigidly fastened or received within the casing 20. However, other constructional solutions are possible as well.

The bag/volume 4 is received preferably within the shell 24 such that it can collapse within the shell 24 when fluid 2 is withdrawn.

The container 3 or bag/volume 4 is preferably closed by a closure 25 as schematically shown in FIG. 4. It has to be noted that the container 3 or closure 25 is still closed in FIG. 4, in particular the conveying element or tube 9 has not been inserted yet.

Further, the FIG. 4 shows the container 3 with still closed venting. In particular, the seal 26, such as a foil or the like, covers or seals the base 22 or venting hole 23 of the container 3 or its casing 20. However, other constructional solutions are possible as well.

When the venting, in particular the seal 26, is open, air or any other gas can flow through the venting hole 23 into casing 20 and through a venting opening 27 into shell 24 so that pressure equalization is possible or achieved. In particular, negative air pressure can be avoided or at least compensated when withdrawing fluid 2 and, thus, collapsing bag/volume 4. However, a throttle effect of the venting hole 23 and venting opening 27 may have different impact on the temporary pressure differences occurring during fluid withdrawal which might result in some variation of the volume of withdrawn doses.

According to an additional aspect of the present invention which focusses in particular on the nebulization of structured fluids, effects due to the viscosity of the fluid (slow initial filing of nebulizer in particular for viscous fluids) can be minimized by pressurizing the fluid 2 during fluid withdrawal in the container 3 as described later in detail. Additionally, effects due to negative pressures occurring during fluid withdrawal in the container 3 can be minimized or avoided by preferably temporarily pressurizing the fluid 2 and/or by temporarily pumping air into the container 3.

In particular, this preferably temporarily pressurizing is effective when priming a nebulizer 1 with a higher viscous fluid 2. For a higher viscous fluid 2, the pressure difference just produced when cocking the nebulizer 1 (i.e. when creating under pressure in the conveying tube 9) might not be sufficient to draw the fluid 2 up the conveying tube 9 and the shear forces in the conveying tube might not be high enough to affect and reduce the viscosity of the (non-Newtonian) fluid sufficiently (so that it can travel into the pressure chamber towards the nozzle 12 under the underpressure generated when cocking). A positive pressure in the container helps/enables that the higher viscous the fluid 2 enters the nebulizer 1/conveying tube 9 when priming the nebulizer 1/filling the nebulizer 1 for the first time.

According to a test example—a commercially available "non-greasy" body lotion with a very high viscosity of about 1000 centipoise at rest could be sprayed with a softmist inhaler/a nebulizer 1 according to FIGS. 1 and 2 in principle. The package description of the body lotion showed the following ingredients: water, paraffinum liquidum, PEG-150, Myristyl Alcohol, Sorbitan Stearate, Cetyl Palmitate, Sorbitan Oleate, isopropyl Palmitate, Octyldodecanol Palmitic acid, Arachidic Acid, Oleic acid, Sodium carbomer, Phenoxyethanol, Linalool, Limonen, BHT, Geraniol, Citronellol, Citral and parfume. The test set-up of the used nebulizer was: spring force 60N, nozzle channels with a width of 8 μm and a of height 5.6 μm). Eventually the tested nebulizer sprayed a constant volume of the emulsion (66% body lotion and 33% water) in a way similar to spraying an aqueous liquid. However, the initial filling of the nebulizer was difficult without additional pressurization of the fluid during priming of the nebulizer: about 20 actuations of the nebulizer were required to achieve a spray of a full dose from a container 3 according to FIG. 4 (used without any pressurization of the fluid within the container 3). Therefore, for spraying of highly viscous fluids (i.e. fluids with viscosities clearly exceeding 100 centipoise) the use of a container 3 in which a pressure is applied to the fluid 2 in the container is preferred.

Preferably, a pressure of 0.05 to 3 bars is applied to the fluid 2 in the container 3 (at least) during the withdrawal of fluid 2 from the container 3 (in addition to the ambient pressure of typically 1,013 bar). Good results have been achieved with pressures of 1-2 bars applied to the fluid/onto a compressible volume containing the fluid 2. Thus fluids of higher viscosity can be sprayed without the use of propellants within the fluid 2. Preferably, the system according to the invention does not comprises a propellant, but pressurizes the fluid 2 in the container mechanically or pneumatically.

The nebulizer 1 preferably comprises an air pump 30 for—in particular temporarily—pressurizing the fluid 2 in the container 3, in particular the bag/variable volume 4 in the container 3, preferably to help collapsing the bag/volume 4 and/or to facilitate withdrawal or sucking of fluid 2 from the container 3.

Figure 5A:
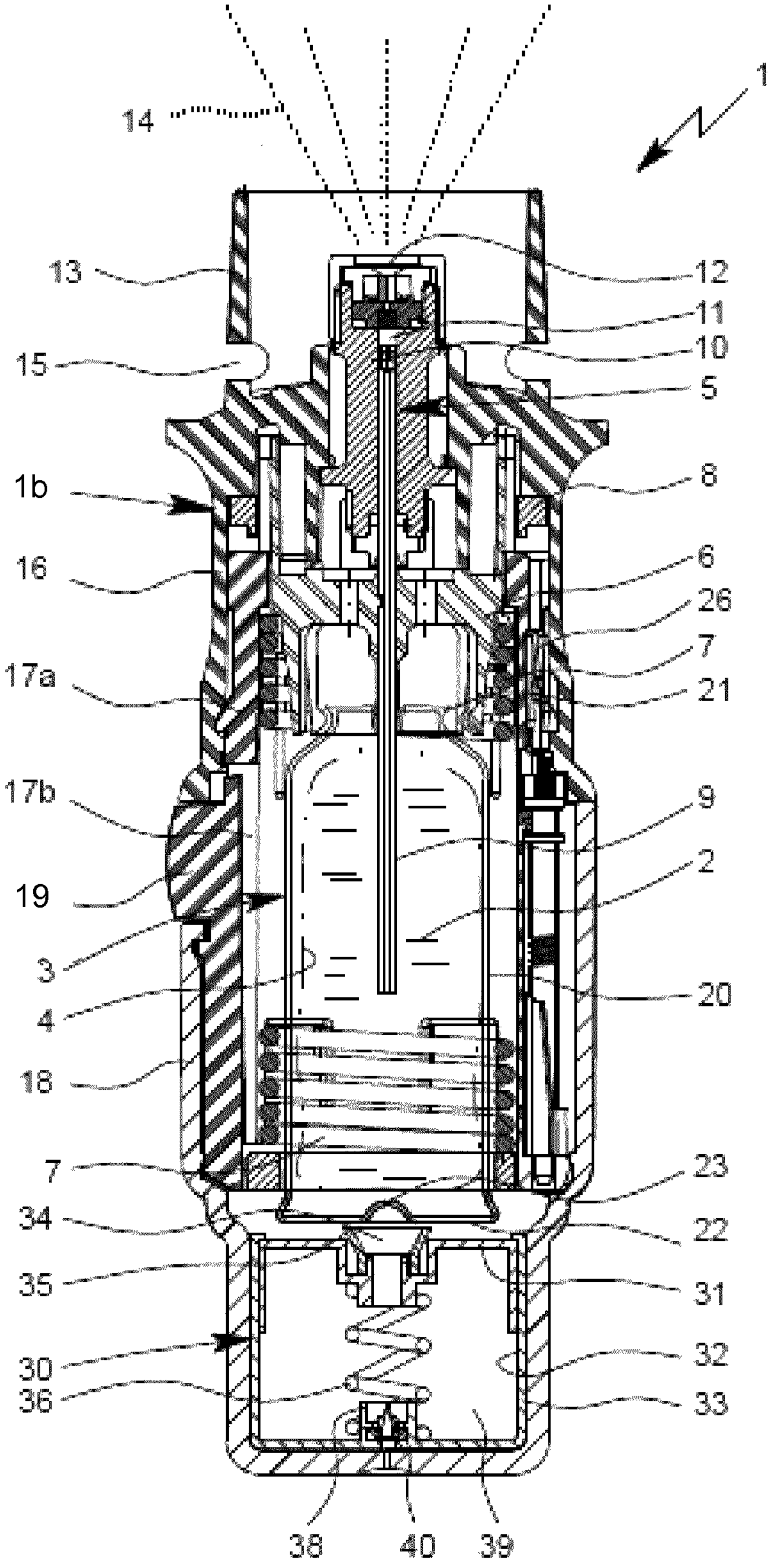
FIG. 5*a* a schematic section of a modified nebulizer (or second embodiment of a nebulizer) in a non-tensioned state.
Figure 5B:
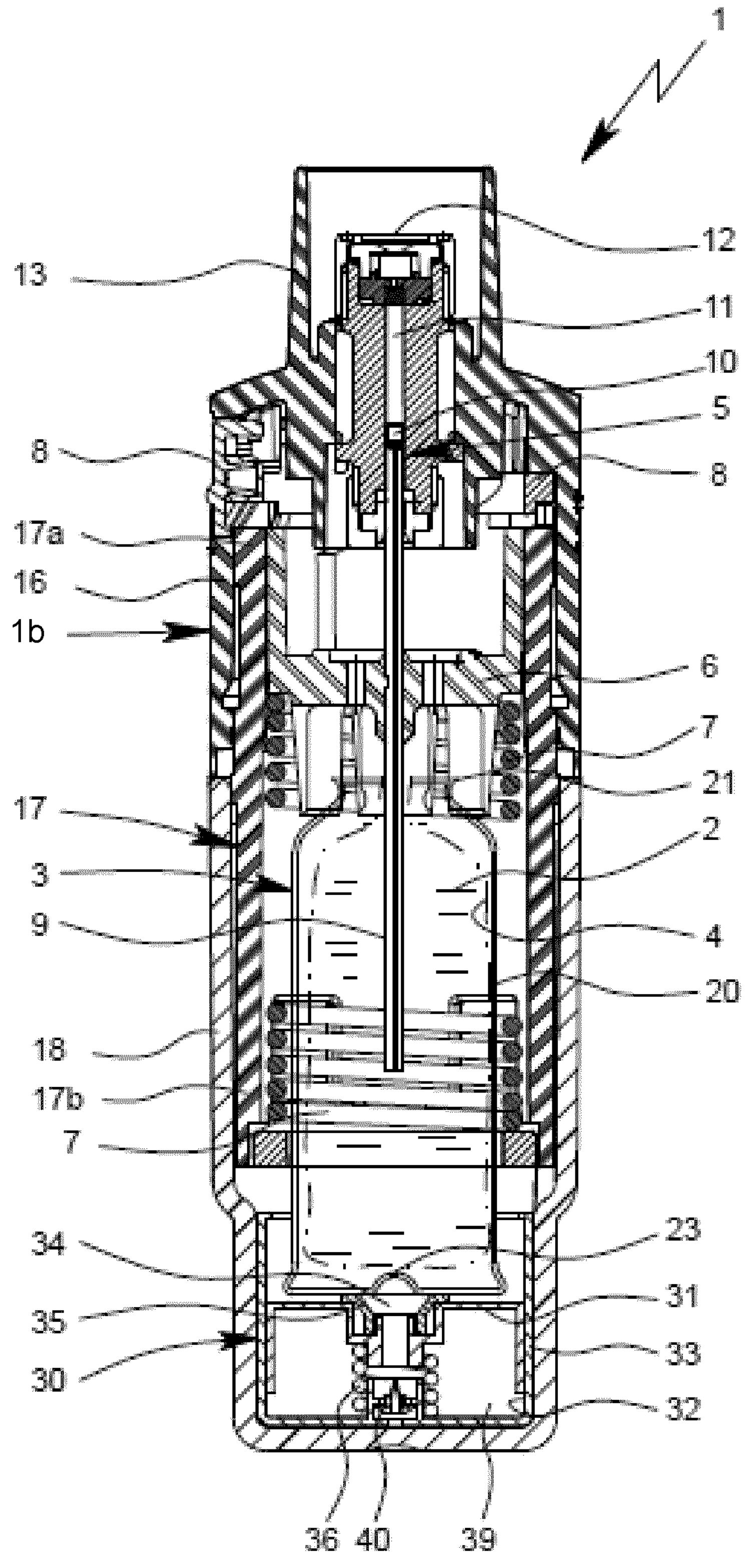
FIG. 5*b* a schematic section, rotated 90° compared with FIG. 5*a*, of the modified nebulizer in a tensioned state.

FIGS. 5*a* and 5*b* show a modified nebulizer 1 similar to the embodiment shown in FIG. 1 and FIG. 2, but additionally comprising an air pump 30. The modified nebulizer 1 is shown in a non-tensioned state (FIG. 5*a*) and in a tensioned state (FIG. 5*b*).

The air pump 30 is formed preferably separately from the container 3.

The air pump 30 is preferably connectable—in particular only temporarily—to the container 3 or its casing 20 or base 22 or venting hole 23.

The air pump 30 is preferably arranged opposite to the fluid pump 5 and/or the fluid outlet or head 21 of the container 3.

The air pump 30 is arranged or located preferably at or in the housing part 18 and/or adjacent to the base 22 of the container 3.

Preferably, the air pump 30 comprises a pump piston 31 and a cylinder 32 cooperating with the pump piston 31. Thus, the air pump 30 comprises or forms a piston/cylinder arrangement for pressurizing the fluid 2 in the container 3 and/or for pumping air into the container 3.

Preferably, the pump piston 31 is cup-like.

Optionally, a sealing can be provided between the pump piston 31 and the cylinder 32. For example, a sealing element, such as an O-ring or the like, could be used. Alternatively or additionally, the inner surface of the cylinder 32 and/or the outer surface of the pump piston 31 can be provided with a glide agent, such as silicone, grease or the like, in order to reduce fiction and/or for sealing.

The cylinder 32 may be formed by the housing part 18 or an element or insert 33 attached to or arranged in the nebulizer 1, the housing 1*b* or—most preferably—the housing part 18.

In the shown embodiment, the insert 33 is fixed in the housing part 18 by press-fit or form-fit or by gluing, welding or the like.

The air pump 30 or pump piston 31 comprises preferably a port 34 and/or seal 35 for pneumatically connecting the air pump 30 to the container 3 or its base 22 or venting hole 23.

Preferably, the seal 35 is arranged at or around the port 34 or forms the port 34 and/or held by the pump piston 31.

Preferably the seal 35 forms an annular lip and/or conical connection portion for sealing against the container base 22 and/or surrounding the venting hole 23 when the container 3 is pneumatically connected to the air pump 30 or vice versa. In this state, the port 34 or seal 35 abuts preferably against the container base 22.

Preferably, the air pump 30, pump piston 31, port 34 and/or seal 35 is arranged centrally and/or below the container 3, base 22 or venting hole 23 and/or in axial alignment with the container 3 or its stroke movement.

The air pump 30 comprises preferably a return spring 36 for returning or biasing the pump piston 31 into its initial position shown in FIG. 5*a*. The pump piston 31 is in this initial or upper position in particular when the nebulizer 1 is not in use or is not tensioned.

Figure 5C:
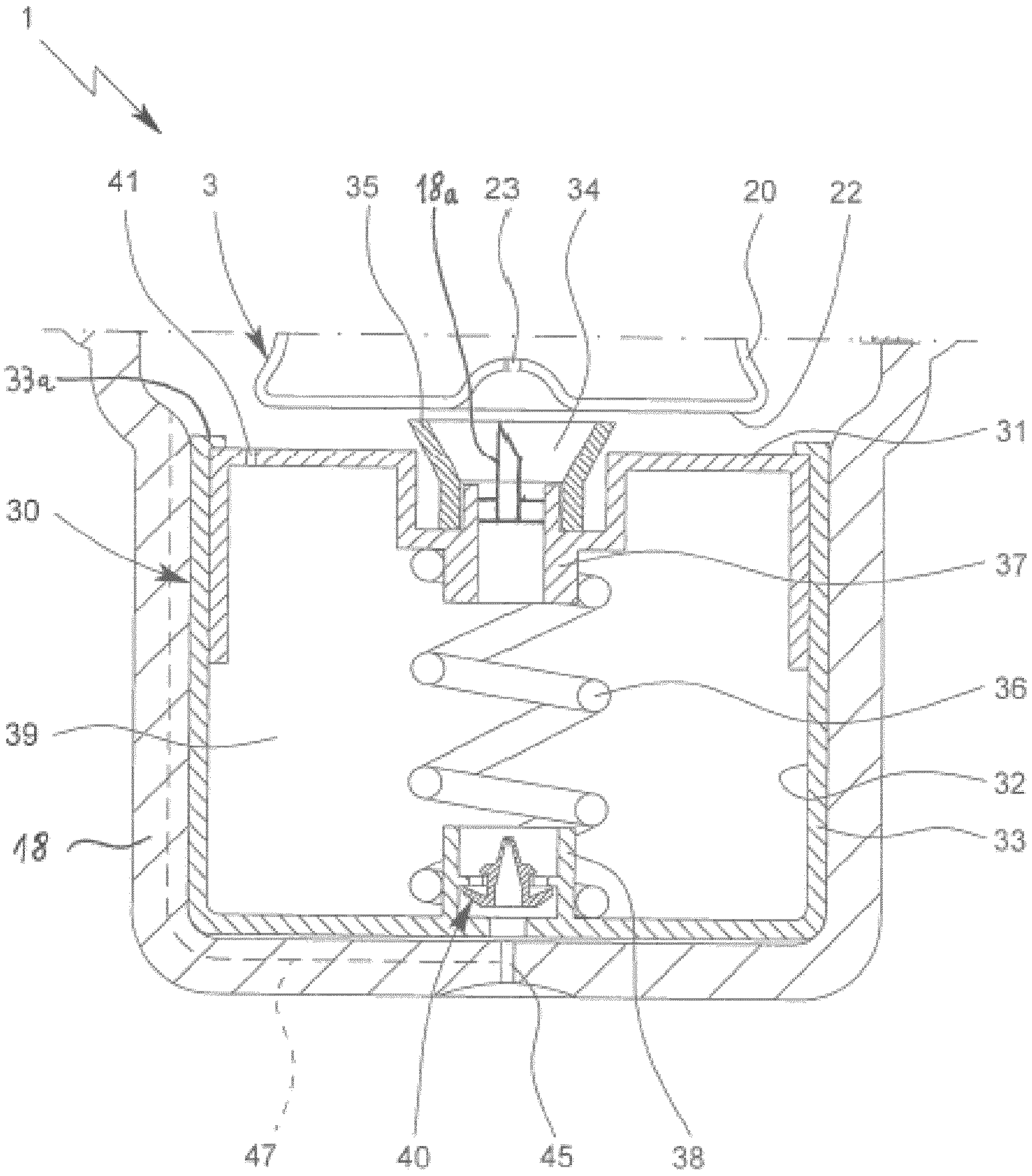
FIG. 5*c* a schematic section of a lower part of the nebulizer with a piston/cylinder arrangement in the non-tensioned state of FIG. 5*a* and FIG. 5*b;*

Preferably, the air pump 30 or insert 33 comprises a stop 33*a* as indicated in FIG. 5*c* for restricting the return travel of the pump piston 31 and/or defining the initial or upper position of the pump piston 31.

In the shown embodiment, the return spring 36 acts between the pump piston 31 and the housing part 18 or insert 33.

Preferably, the return spring 36 is formed by a helical spring and/or extends in axial direction or in the direction of stroke movement of the container 3 and/or is arranged centrally in the nebulizer 1, below the container 3 and/or in the air pump 30.

Preferably, the pump piston 31 comprises a bearing part 37, such as a recess or protrusion, for holding an associated end of the return spring 36.

Preferably, the insert 33 or housing part 18 comprises a bearing part 38, such as a recess or protrusion, for holding the associated end of the return spring 36.

The air pump 30 comprises a pump chamber 39 formed between the pump piston 31 and the cylinder 32/insert 33. In particular, the volume of the pump chamber 39 is defined or varied by the position or movement of the pump piston 31.

FIG. 5*b* shows the nebulizer 1 in the tensioned state with the pump piston 31 in the actuated or depressed position. In this position, the pump piston has been moved (further) into the cylinder 32 or insert 33 or housing part 18 and air contained in the pump chamber 39 has been compressed and/or delivered into the container 3.

The air pump 30 works preferably mechanically.

Preferably, the air pump 30 is arranged in the center of the nebulizer 1 and/or below the container 3 and/or axially aligned with the nebulizer 1 and/or container 3.

The air pump 30 or pump piston 31 is preferably actuated by the movement of the container 3 within the nebulizer 1 and/or the stroke-like movement or tensioning movement of the container 3.

In particular, the container 3 or its base 22 is spaced from the air pump 30, pump piston 31, port 34 or seal 35 when the nebulizer 1 or container 3 is in the non-tensioned state or after nebulizing a dose.

Thus, the air pump 30 is temporarily open and/or (pneumatically) disconnected from the container 3 or vice versa. In particular, the aeration or venting hole 23 is open or uncovered in the non-tensioned state so that free compensation is possible between the pressure within the container casing 20 and the outer atmosphere.

Preferably, the stroke-like movement or tensioning movement of the container 3 controls opening or filling of the air pump 30.

When tensioning the nebulizer 1, the container 3 is moving towards and/or relative to the air pump 30 or its pump piston 31. After a first (shorter) part of the tensioning movement, the container 3 or its base 22 (pneumatically) connects with the air pump 30 or its pump piston 31 or port 34/seal 35. During the further or second (larger) part of the tensioning movement, the air pump 30 or pump piston 31 is actuated or depressed so that an air pressure is generated which can directly act—here preferably via the port 34/seal 35 and the venting hole 23—on the fluid 2 in the container 3 or, more precisely, on the bag or variable volume 4 within the container 3. In other words, the air pump 30 pumps air into the space between the bag or variable volume 4 and the casing 20/shell 24.

Preferably, the air pump 30 comprises a total volume and/or a pump volume of more than 0.1 $cm^3$, in particular of more than 0.5 $cm^3$, and more preferably of more than 1.0 $cm^3$. In particular, the pump volume is between 1 and 4 $cm^3$.

Preferably, the pump volume of the air pump 30, i.e. here the volume difference between the uncompressed state and the compressed state of the air pump 30 and/or the minimum volume of air pumped into the container 3 by the air pump 30 during each actuation, is more than 3%, in particular more than 5%, most preferably more than 8%, and/or less than 50%, preferably less than 40%, most preferably less than 30%, of the air volume of the container 3 after withdrawing the maximum number of doses of fluid 2 or all fluid 2.

Preferably, the air pump 30 provides a defined or limited pressure increase (depending on the maximum air pressure provided by the air pump 30) in the container 3 (in particular in the space between the inner container and the casing 20 and/or shell 24) or acting on the fluid 2/variable volume 4 of more than 25 hPa, preferably more than 40 hPa, and most preferably of more than 50 hPa or 100 hPa, in particular just after tensioning the nebulizer 1.

The pressure increase mentioned above might depend on the state of collapsing of the bag or on the compression of the variable volume 4. The above values apply in particular when the bag is completely collapsed (or the variable volume is completely compressed) and/or when the maximum number of withdrawn doses of fluid 2 is reached.

The pressure acting on the bag/variable volume 4 in the container 3 increases during the second part of the tensioning movement of the container 3, i.e. during the actuation of the air pump 30, until the tensioned state or end position and the maximum air pressure are reached. This pressure increase helps of facilitates withdrawal or sucking of fluid 2 from the container 3 or its bag/variable volume 4.

Preferably, the nebulizer 1 or air pump 30 comprises at least one air leakage or valve 40 for controlling or limiting the (maximum) air pressure and/or for aerating the air pump 30 or its pump chamber 39 and/or for preventing any underpressure (negative pressure with respect to the ambient pressure) in the air pump 30 or pump chamber 39. However, the valve 40 is only optional and can be omitted.

Preferably, the pressure decreases again, in particular automatically, during the nebulization process (preferably due to movement of the pump piston 31 from its actuated position into the initial position or due expansion of the pump chamber 39 caused by the return spring 36 or due to disconnection of the air pump 30 or port 34 from the container 3 during the nebulization movement of the container 3) and/or preferably even already in the tensioned state (preferably due to the air leakage and/or valve 40).

Therefore, the bag/variable volume 4 or fluid 2 is pressurized only temporarily in the container 3, preferably mainly only during the tensioning movement and/or preferably primarily only during withdrawal of a dose of fluid 2 from the container 3 or its bag/volume 4.

After withdrawing or sucking fluid 2 from the container 3 or its bag/volume 4, the nebulizer 1 is in the tensioned or cocked state and/or is ready for dispensing/nebulization.

In the tensioned or cocked state, the air pressure and, thus, the pressurization of fluid 2 decreases (when the nebulizer is held in the tensioned or cocked state for a longer time) and, preferably, is terminated, in particular automatically, due to the air leakage, e.g. between the pump piston 31 and a cylinder 32 and/or between port 34/seal 35 and container base 22. To achieve a desired leakage, there can be provided radial play between the pump piston 31 and the cylinder 32 and/or a respective leakage channel or passage 41, e.g. in the seal 35 or valve 40 or pump piston 31.

Figure 5D:
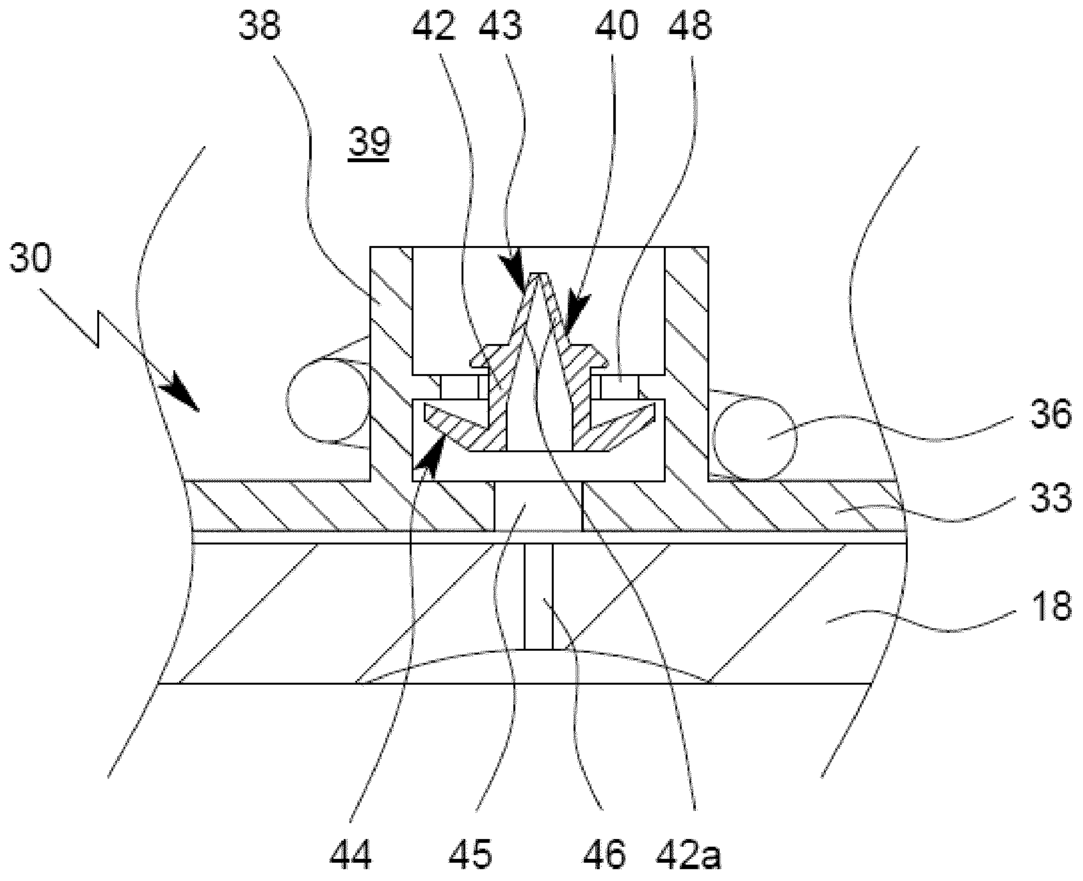
FIG. 5*d* a partial enlargement of FIG. 5*c* illustrating a preferred construction of a valve.

FIG. 5*c* shows in a partial enlargement of FIG. 5*a* the air pump 30 in the lower part of the nebulizer 1/housing part 18. FIG. 5*d* shows an enlargement of FIG. 5*c* in the area of the valve 40.

In the shown embodiment, the air pump 30 or pump piston 31 is preferably provided with the leakage passage 41 as schematically shown in FIG. 5*c*. However, this leakage passage 41 is optional.

Preferably, the leakage passage 41 or any other air leakage, such as the optional/preferred radial play between the pump piston 31 and the cylinder 32, forms a throttle which is dimensioned such that the flow resistance is sufficiently high to create a sufficiently high air pressure during the tensioning stroke and is sufficiently low so that pressurized air can escape relatively quickly in the tensioned state from the pump chamber 39 into the housing 1*b* and/or environment so that the air pressure is quickly decreased in the tensioned state to avoid any undesired fluid flow in the tensioned state of the nebulizer 1 before firing (actuating blocking element 8 to initiate nebulization).

After actuating or firing the nebulizer 1, preferably by actuating element 8 or pressing button 8*b*, the pressure generator or fluid pump 5 pressurizes and dispenses the previously withdrawn dose of the fluid 2 while the container 3 is moving in opposite direction and finally retracting from the air pump 30 and/or pump piston 31/port 34/seal 35.

The return spring 36 and/or any other return means biases or moves the pump piston 31 preferably back into its initial position. This ensures a defined operation of the air pump 30 and/or supports the dispensing stroke and/or prevents or reduces the occurrence of any negative force or holding effect acting on the container 3 during the dispensing stroke, i.e. during an upward movement starting from the position shown in FIG. 5*b*.

The air pump 30 may be provided or connected with the valve 40 allowing prompt and/or easy re-filling of the air pump 30 and/or preventing any underpressure in the air pump 30, e.g. during the dispensing or actuation stroke of the nebulizer 1, so that any negative influence of the air pump 30, such as a holding force acting opposite to the dispensing movement of the container 3, is securely prevented.

In FIGS. 5*c* and 5*d*, the valve 40 is shown, but it is only optional, i.e. the valve 40 could be omitted.

In the preferred embodiment, the valve 40 comprises in particular a valve element 42 which is preferably formed as a unitary plastic part.

The valve 40 or valve element 42 forms or comprises preferably an inlet, duckbill or one-way/check valve 43 which opens to avoid or at least minimize any underpressure in the air pump 30 or pump chamber 39 during the tensioning stroke, i.e. when the pump piston 31 moves back from its actuated position shown in FIG. 5*b* to its initial position shown in FIGS. 5*a* and 5*c*.

Preferably, the valve 40 or valve element 42 or inlet valve 43 comprises—in particular two—flexible portions 42*a* as schematically indicated in FIG. 5*d* (preferably the portions 42 have two flat areas that can assume a duckbill form in the closed position shown in FIG. 5*d* wherein the free ends of the portions 42*a* contact each other to close valve 43).

The valve 40/43 and, in particular, the portions 42*a* open preferably very easily (i.e. at very low pressure difference between the ambient pressure and the pressure in the pump chamber 39) by flexing apart from each other in order to allow ambient air to flow into the pump chamber 39 in order to prevent any underpressure in the pump chamber 39. With other words, the valve 40 and, in particular, the portions 42*a* form preferably the inlet valve or check valve 43 in the present embodiment.

Preferably, the valve 40/43 and, in particular, the portions 42*a* can return to its closed position automatically, preferably due to a restoring force, and/or already due to a low pressure difference with higher pressure in the pump chamber 39 than in the environment.

During the nebulizing stroke, the return spring 36 moves the pump piston 31 starting from the actuated position back into its initial position. During this return travel, the air pump 30 or pump piston 31 keeps the seal 35 in contact with the container base 22 until the initial position and/or stop 33*a* is reached. During this return movement, the pump chamber 39 expands and would generate a significant underpressure so that aeration is advantageous. In particular, the aeration or inlet valve 43 prevents the occurrence of any (relevant) underpressure during this return travel or movement.

The valve 40 or inlet/check valve 43 is connected to the atmosphere preferably via an opening 45, here formed in the optional insert 33, and/or via a channel 46 which is preferably formed in the housing part 18 and may open to the bottom or environment.

Alternatively or additionally, a channel 47 may be formed in the housing part 18 as schematically shown by dashed line in FIG. 5*c*, and/or in the insert 33 for fluidically connecting the inside of the nebulizer 1 or its housing 1*b* with the valve 40 or inlet/check valve 43 to allow ventilation or aeration of the air pump 30 or its pump chamber 39, namely to allow (only) air flow into the pump chamber 39.

The valve 40 or valve element 42 or another valve of the nebulizer 1 or air pump 30 comprises or forms preferably a control valve 44 for controlling or limiting the air pressure acting on the fluid in the container 3 and/or provided or reached by the air pump 30.

In the shown embodiment, the control valve 44 is formed preferably like an umbrella and/or covers one or more outlet openings 48 as schematically shown in FIG. 5*d*.

The control valve 44 opens preferably when a predetermined or desired air pressure is reached in the air pump 30 or pump chamber 39. Thus, a defined or maximum air pressure is provided for pressurizing the fluid 2 in the container 3.

The control valve 44 opens and closes preferably automatically, in particular in response to a pressure difference between the environment and the pump chamber 39 so that ambient air (or air from the inside of the nebulizer 1 with ambient pressure) can flow into the pump chamber 39, preferably with a very low or non-relevant flow resistance. In the opposite flow direction, the control valve 44 preferably closes and/or prevents any flow. However, the control valve 44 could also allow a defined leakage flow in this opposite direction to form the air leakage and/or so that e.g. the leakage passage 41 can be omitted.

The preferred controlling or limiting of the air pressure provided by the pump 30 to a maximum air pressure (i.e. to a maximum value above the ambient air pressure) results in the advantage that the fluid 2 in the container 3 is pressurized with a desired and/or predetermined pressure independent from the filling level of the container 3, i.e. independent from the air volume of the container 3.

In the shown embodiment, the valve 40, the inlet/check valve 43 and/or control valve 44 are located preferably in or at the pump chamber 39 or bearing part 38. However, other constructional solutions are possible as well.

Preferably, the valve 40 or its valve element 42 forms both, the inlet/check valve 43 and the control valve 44, to simplify the construction.

However, is also possible that the seal 35 forms the valve 40, inlet/check valve 43 and/or control valve 44 or vice versa.

In the embodiment shown in FIG. 5*c*, the optional aeration device 18*a* is preferably arranged within or adjacent to the port 34 and/or seal 35 and/or at or adjacent to the pump piston 31 and/or bearing part 37. In particular, the aeration device 18*a* or its piercing element 18*b* (for instance in form of a preferably hollow needle) is held by radial ribs, an insert or the like cooperating or connected with the pump piston 31, bearing part 37 or the like.

In the shown embodiment, the aeration device 18*a* is arranged preferably at or within the port 34, seal 35 and/or bearing part 37, but allows a sufficient or unrestricted air flow therethrough. For this purpose, only view radial ribs might be provided and/or the aeration device 18*a* or its needle can be hollow.

Figure 6:
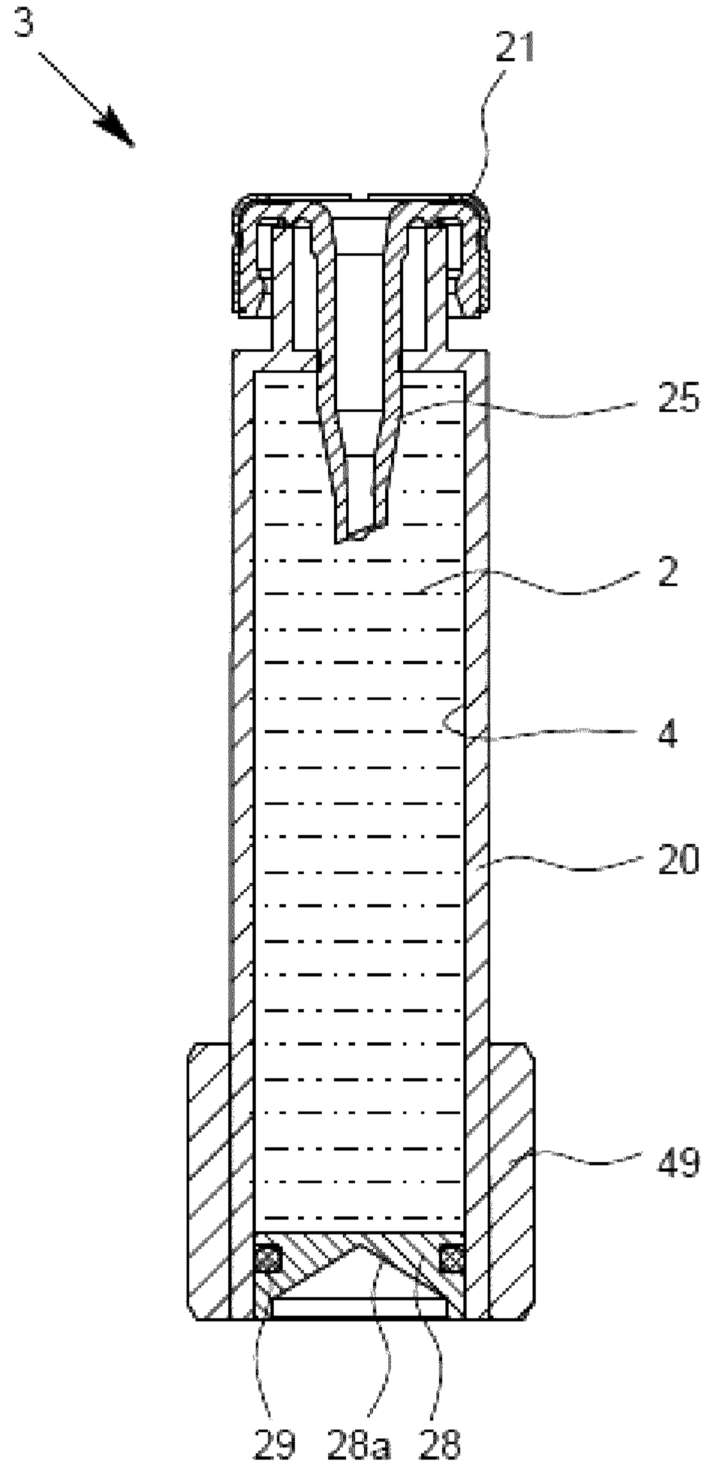
FIG. 6 a schematic section of a second embodiment of the container for the nebulizer.

FIG. 6 shows in a schematic section a second embodiment of the container 3. Here, the variable or collapsible volume 4 for the fluid 2 is formed or limited preferably by the (outer) casing 20 and a moveable element or piston, hereinafter called fluid piston 28.

Preferably, the fluid piston 28 is moveable axially and/or within the container 3 or casing 20.

Preferably, the container 3 is provided with a seal 29 acting between the fluid piston 28 and the casing 20. In particular, the seal 29 is formed as a ring or lip and/or held by the fluid piston 28. However, other constructional solutions are possible as well.

FIG. 6 shows the container 3 in a completely filled state where the fluid piston 28 is in its initial position before withdrawing any fluid 2 from the container 3. In particular, the initial position is adjacent to or at the base 22 or axial end of the container 3 or casing 20 opposite to the outlet or head 21. Thus, a maximum filling volume of the container 3 can be realized.

When withdrawing fluid 2, the piston 28 moves axially towards the outlet or head 21, here in the representation of FIG. 6 upwards. This is in particular advantageous, when withdrawing a viscous fluid from the container: The pressure on the fluid is directed towards the outlet of the container 3 and thus into the direction in which the initial filling of the nebulizer 1 takes place. This alignment of flow direction and pressure impaction helps the initial filling of the nebulizer with fluid, so that for instance the number of additional priming actuations which are needed for forcing a viscous fluid along in the nebulizer may be reduced.

The container 3 according to the embodiment shown in FIG. 6 comprises preferably also an at least essentially cylindrical form and/or a similar casing 20, head 21 and/or closure 25 as the container according to the embodiment of FIG. 4.

Preferably, both types or embodiments of containers 3 can be used in the nebulizer 1 shown in FIGS. 5*a* and 5*b*, in particular both types or embodiments of containers can be used with an air pump 30. The nebulizer 1 or the air pump might require slight modifications depending on the specific embodiment of the container to be used: For instance—contrary to the container 3 of the second embodiment—the container 3 of the first embodiment as shown in FIG. 4 (i.e. a container with a bag as a collapsible inner volume 4 and with a venting hole 23 to be opened for the withdrawal of fluid) requires the presence of an aeration device 18*a*/piercing element 18*b*.

If the container 3 according to the second embodiment shown in FIG. 6 is used, the seal 35 of the air pump 30 should be adapted so that it abuts against the end or base 22 of the container 3, and not within the opening for the fluid piston 28.

In particular, the container 3 may comprise a modified end 49, here shown in FIG. 6 as an additional part, ring, sleeve or the like attached to the casing 20. This modified end 49 may form an annular end face or base 22 of the container 3 with which the seal 35 may cooperate.

However, other constructional solutions are possible. For example, the container 3 might be provided with the seal 35 instead of air pump 30 or pump piston 31.

Alternatively, the pump piston 31 can be directly connected or connectable with the container 3 or its base 22. In this case, the return spring 34 can be omitted similar to the second embodiment described below.

In the following, a third embodiment of the nebulizer 1 will be described with reference to the further drawings, wherein the description will focus on differences and new aspects and features so that the previous description shall apply in addition or in a similar manner even if not repeated.

Figure 7:
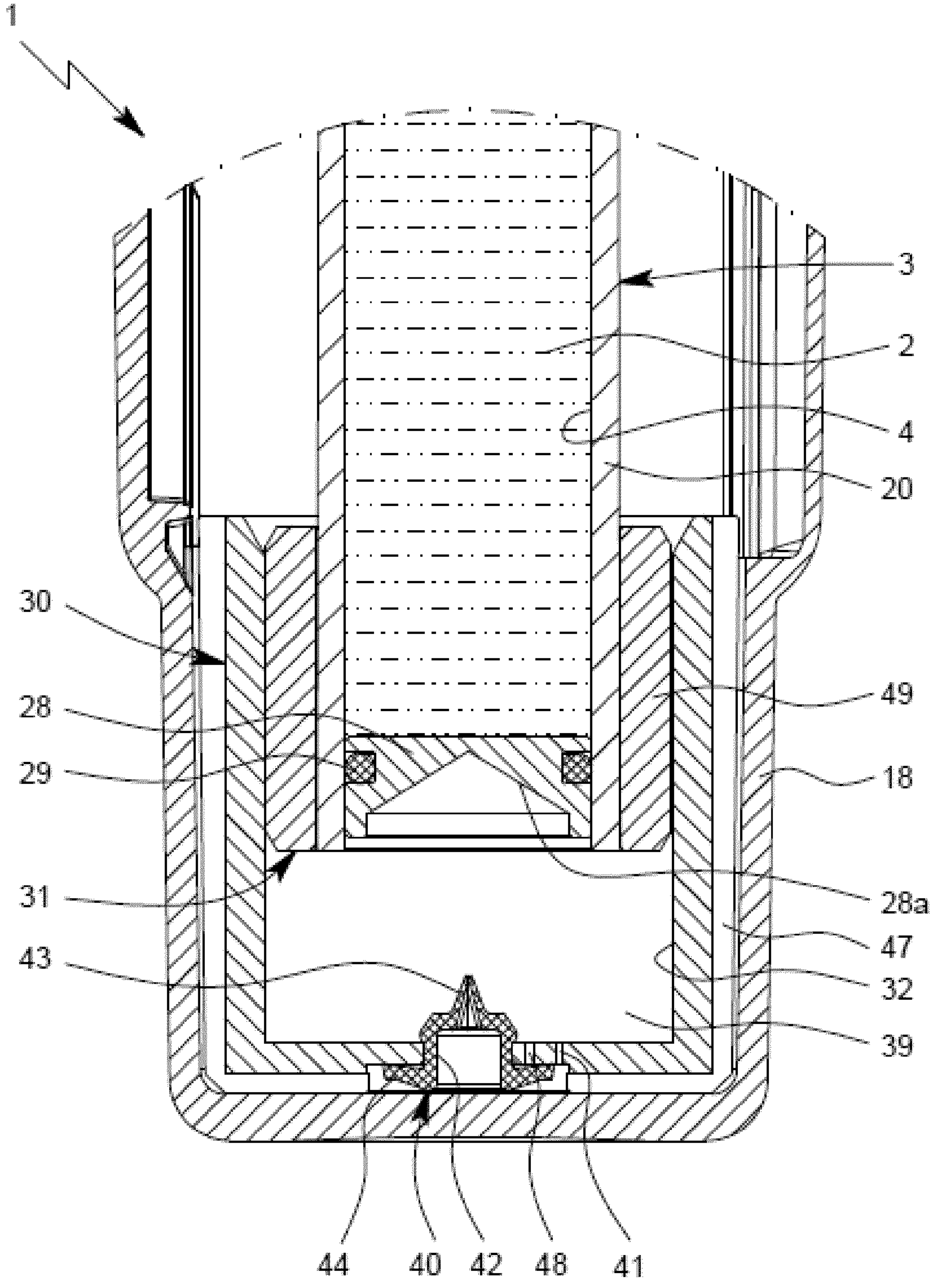
FIG. 7 a schematic section of a lower part of the nebulizer according to a third embodiment in a non-tensioned state.
Figure 8:
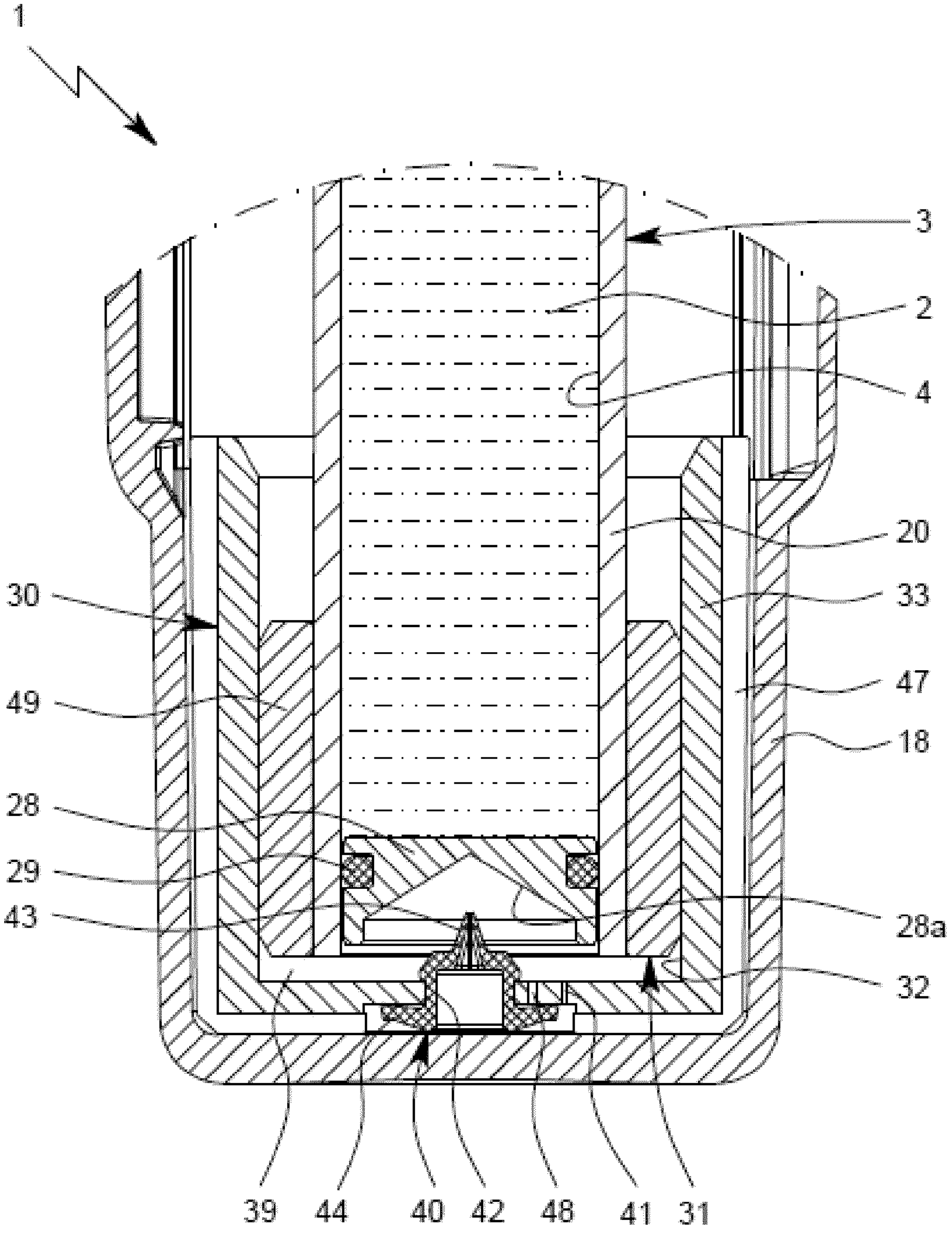
FIG. 8 a schematic section of the lower part of the nebulizer similar to FIG. 7, but in a tensioned state.

FIG. 7 shows a lower portion of the third embodiment of the nebulizer 1 with the container 3 in the non-tensioned state of the nebulizer 1, i.e. an enlargement similar to FIG. 5*c*, but with a modified air pump 30. FIG. 8 shows the nebulizer 1 and container 3 according to the third embodiment in a similar section, but in the tensioned state.

The nebulizer 1 according to the second embodiment uses the container 3 according to the second embodiment shown in FIG. 6.

In a third embodiment, the container 3 forms or is used as the pump piston 31. The container 3 cooperates with the cylinder 32 preferably formed by the housing part 18 or insert 33 so that a piston/cylinder arrangement for pumping air into the container 3 to help withdrawing the fluid 2 in doses from the container 3 is formed.

Here, the pump chamber 39 is formed between the container 3 or its base 22 and the cylinder 32/insert 33.

The container 3 or its modified end 49 is moveable or guided within the cylinder 32, preferably with very low friction and/or a (little) radial play forming a desired air leakage and making it possible to avoid the optional defined leakage passage 41.

In the third embodiment, the air pump 30 acts directly on the fluid piston 28 in order to pressurize the fluid 2 in the variable volume 4 of the container 3.

In the third embodiment, the valve 40 is preferably constructed similar as in the second embodiment and/or provides the same functionality.

In the third embodiment, the aeration channel 47 is formed preferably in the insert 33.

The container 3 or fluid piston 28 comprises preferably a recess 28*a* so that the valve 40 arranged on the bottom or base of the pump chamber 39 can protrude into the recess 28*a* in the tensioned state when the container 3 is completely filled, i.e. when the fluid piston 28 is in its axial end position at or adjacent to the container base 22.

Generally, the diameter of the pump chamber 39 or cylinder 32/pump piston 31 is preferably larger than the diameter of the bag/volume 4 in the container 3 to ensure a great pressure increase/amplification and/or high pump volume.

The present invention or air pump 30 prevents that any or at least any relevant underpressure can occur in the fluid 2 in the container 3 when a dose of the fluid 2 is withdrawn or sucked from the container 3. Thus, it can be ensured that always the same volume is withdrawn from the container 3.

In particular, the shown or proposed containers 3 allow an adaptation of the variable or collapsible volume 4 for the fluid 2 (here by collapsing the bag or movement of the fluid piston 28) in response to any pressure difference, in particular in response to any underpressure acting on the fluid 2 in the container 3 or volume 4. For the adaptation of the volume 4, in particular for collapsing the bag or moving the fluid piston 28, a certain pressure difference must be applied in order to overcome any inertia and/or friction or adhesion. The preferably temporary or only short-term pressurization of the variable volume 4, preferably by means of the air pressure or air pump 30, helps or supports to achieve the desired/required pressure difference to decrease the volume 4. Thus, any underpressure can be avoided in the volume 4 during the withdrawal of a dose of the fluid 2 from the container 3.

Preferably, a pressure pulse—in particular provided by the nebulizer 1 or air pump 30—acts on the variable volume 4 or the fluid 2 in the container 3 at the beginning and/or during the tensioning of the nebulizer 1 and/or withdrawal of fluid 2 from the container 3. This helps withdrawing the fluid 2 in doses from the container without forming or growing of any gas bubble within the fluid 2/container 3.

FIG. 9 shows in a partial section similar to FIG. 7 the nebulizer 1 according to the third embodiment with inserted container 3 in the non-tensioned state with a modified valve 40. In this modified version, the valve 40 is preferably dome-like shaped.

The modified valve 40 provides preferably the same functionality as the previously described versions and/or controls or limits the (maximum) air pressure in the pump chamber 39 and/or allows ambient air to flow into the pump chamber 39 in order to prevent any underpressure in the pump chamber 39.

Preferably, the valve element 42 of the modified valve 40 comprises slits and/or flexible portions 42*a* (preferably the portions 42*a* form sectors of a circle in top view of the valve element 42).

The valve 40 and, in particular, the portions 42*a* open preferably very easily (i.e. at a very low pressure difference between the ambient pressure and the pressure in the pump chamber 39) towards the interior of the air pump 30 or pump chamber 39 in order to allow ambient air to flow into the pump chamber 39 in order to prevent any underpressure in the pump chamber 39. With other words, the valve 40 and, in particular, the portions 42*a* form preferably the inlet valve or check valve 43 described above.

Preferably, the valve 40 and, in particular, the portions 42*a* can flex or open to the outside and allow air to escape from the pump chamber 39 only if the pressure inside the pump chamber 39 is significantly higher than the ambient air pressure, i.e. only if the pressure difference reaches or exceeds a maximum value corresponding to a maximum air pressure. With other words, the valve 40 and, in particular, the portions 42*a* form preferably the control valve 44 as described above.

The nebulizer 1, housing part 18, air pump 30 or valve 40 is provided preferably with a support/throttle element 50, such as a ring with a radial slit or the like, in order to support or secure the valve element 42, in particular from below and/or in a respective opening in the insert 33, and/or to throttle the inlet and/or outlet air path. However, other constructional solutions are possible as well.

In the shown embodiment, the air passage 41 is not realized by a separate or additional bore or hole e.g. in the insert 33 as shown in FIGS. 7 and 8 or in the pump piston 31 as indicated in FIG. 5*c*, but by a preferred and defined radial play between the cylinder 32 on one hand and the pump piston 31/modified end 49 on the other hand.

As in the previous embodiments, the leakage passage 41 allows a relatively slow (in comparison to the pressure increase during the tensioning movement or actuation of the air pump 30) pressure compensation or equalization between the pump chamber 39 and the ambient air pressure, preferably within about 2 to 10 s, most preferably within about 4 to 6 s.

Further, the radial play avoids or minimizes the friction between the container 3 and the cylinder 32 so that a negative force acting against the nebulization movement is avoided as such negative force might negatively influence the nebulization process.

Generally, it is preferred that the absolute maximum air pressure of the air pump 30 or pump chamber 39 (this pressure is reached just when the nebulizer 1 reaches the tensioned state) returns automatically and/or gradually to the ambient air pressure within 10 s, in particular about 8 s, preferably about 6 s or less. This return time depends on the dimension of the air leakage and/or construction of the valve 40.

Preferably, the (relative) maximum air pressure (i.e. the pressure difference between the air pressure in the air pump 30/pump chamber 39 and the environment) is more than 80 mbar, in particular more than 100 mbar, and/or less than 300 mbar, in particular less than 200 mbar.

For containers 3 comprising a fluid piston 28 or the like, friction generally occurs between the fluid piston 28 and the casing 20/cylinder 32. This is known as "glide force". When a dose of fluid 2 is withdrawn from the container 3, an underpressure occurs. This underpressure "sucks" the fluid piston 28 inwards.

When the container 3 has not been used for a long time an additional friction force known as "break loose force" can occur so that the fluid piston 28 sticks to the cylinder wall. By means of the air pump 30 and/or the application of air pressure during the tensioning, the glide force and in particular the break loose force can be overcome.

Preferably, the container 3, its casing 20 or the cylinder 32 can be made of glass or provide an inner surface of glass in order to reduce the friction and in particular the glide force and/or break loose force.

Alternatively or additionally, the inner surface of the cylinder 32 can be provided with a glide agent, such as silicone, and/or a baking of silicone or the like, in order to reduce the friction and in particular the glide force and/or break loose force.

In particular, a uniform coating preferably of oil can be produced by baking. Such a film is more stable on the inner surface of the cylinder 32 and remains in place even when the container 3 is filled with the fluid 2.

Preferably, the container 3 or casing 2 or inner surface of the cylinder 32 is baked or covered with silicone. This is done preferably just before filling the container 3 with the fluid 2. Prior to the filling, the baked container 3 is preferably sterilized.

The use of an air pump 30 (especially with air pressure control means i.e. valve 40) allows, supports or ensures a very precise metering and/or facilitates to keep the volume of the dispensed doses highly constant (even for containers from which the larger part of the fluid content has already been withdrawn). Further, the formation or growing of any gas bubble within the fluid 2 or bag/variable volume 4 can be prevented.

Figure 10:
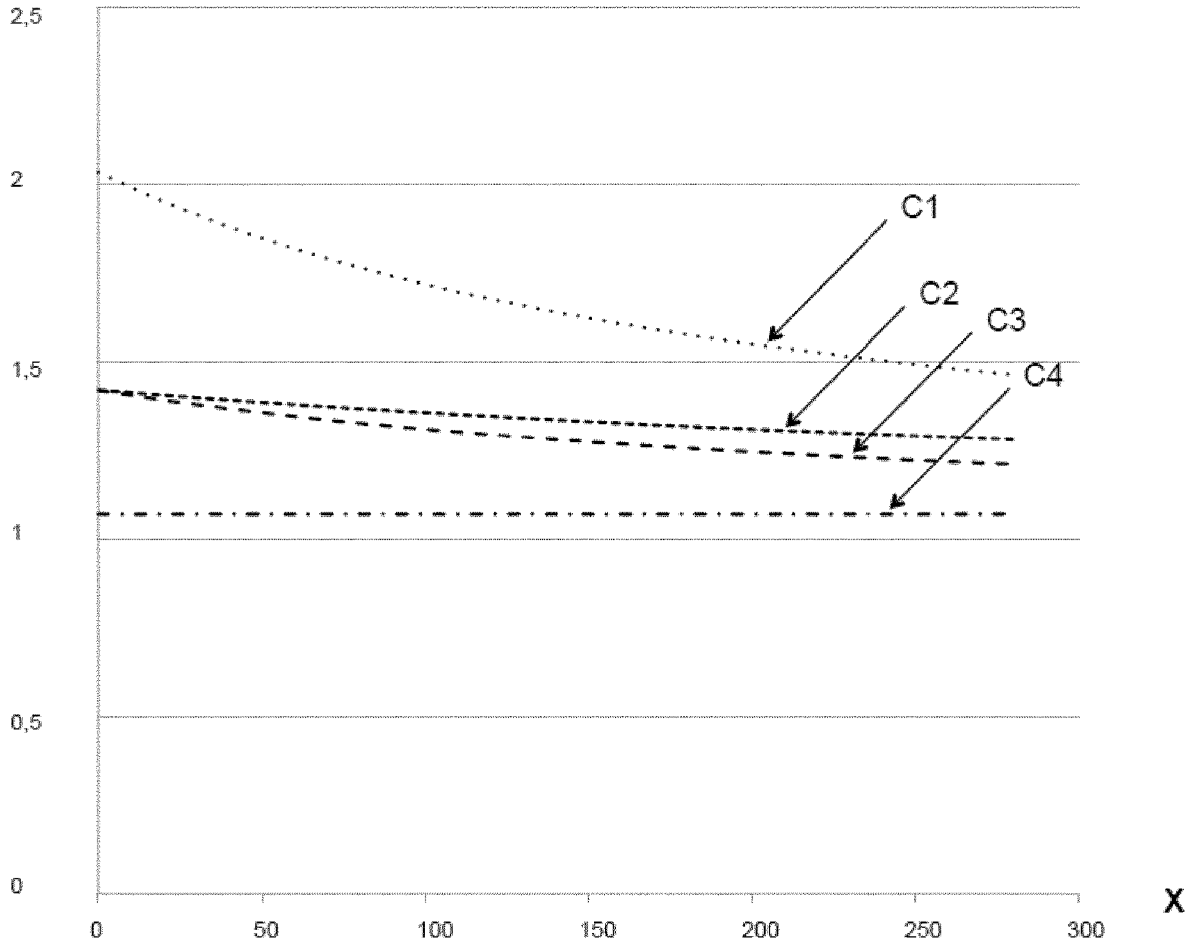
FIG. 10 a diagram of the pressure progression as a function of actuations.

In a diagram FIG. 10 schematically shows different pressure progressions as a function of actuations (number of dispensed doses of fluid 2) for the nebulizer 1/air pump 30 according to the second embodiment (shown in FIGS. 5*a*, 5*b* and 5*c*) with the container 3 according to the first embodiment (shown in FIG. 4).

The X axis denotes the number of actuations. The axis starts with "0" which means that any dose of fluid 2 has not been withdrawn or dispensed from the container 3, i.e. the container 3 or its volume 4 is completely filled at this point.

The Y axis denotes the pressure in bar. The pressure of 1,0 bar represents or corresponds to the normal pressure (ambient air pressure) in the calculation.

As already mentioned, a certain pressure difference must be applied to overcome any inertia and/or friction or adhesion to ensure the desired collapse of the variable volume 4, here the bag, of the container 3 so that any underpressure in the variable volume 4 can be avoided or at least minimized during withdrawal of a dose of the fluid 2 and/or so that a very precise/defined and in particular constant volume of fluid 2 is withdrawn during each tensioning stroke or pump process or loading of the fluid pump 5. This pressure difference is particularly between 40 mbar and 100 mbar and has been assumed to be 70 mbar in the shown diagram. This is reflected by curve C4 which shows the absolute pressure corresponding to the desired or assumed pressure difference of 70 mbar which should be reached or exceeded to ensure or facilitate precise metering as explained.

The curves C1 to C3 show different calculations of the pressure progression under different conditions. The progression of curve C1 has been confirmed by respective experiments (without valve 40/43). Further, the values used for the calculations correspond to the sample used for experiments.

The curves C1 to C3 show the maximum air pressure that is reached during an actuation or tensioning.

In all cases, the air volume of the container 3 is about 2 ml at the beginning and the pump volume of the air pump 30 is about 3.5 ml.

For curve C1, the total volume of the air pump 30 is about 5 ml and the volume of each dose of withdrawn fluid 2 is 15 microliters.

For curve C2, the total volume of the air pump 30 is about 10 ml and the volume is 15 microliters for each dose of fluid 2 that is withdrawn during each actuation. In particular, the effective length of the cylinder 32/insert 33 is doubled/varied in order to double/vary the total volume of the air pump 30.

For curve C3, the same volume, i.e. about 10 ml, is the total volume of the air pump 30, wherein the volume of each dose of fluid 2 is 30 microliters.

It is visible that all three curves C1 to C3 lie significantly above the desired minimum curve C4 so that the desired minimum pressure (difference) is reached or exceeded and precise metering can be expected or supported. I.e. in this set-up, even initially adding a pressure of 0.4 bar (above ambient pressure) is sufficient for supporting precise metering (minimum additional pressure in this set-up being more than 0.07 bar). Preferably, the additional pressure ranges between 0.2 bar (three times minimum additional pressure) and 1 bar or more.

The difference between curve C1 on one hand and curves C2 and C3 on the other hand shows that the total volume of the air pump 30, of an air buffer (the total air volume, i.e. sum of air pump 30 and completely filled container 3 minus the pump volume of the air pump 30, i.e. about 3.5 ml for C1 and about 8.5 ml for C2 and C3) and/or of both, the air pump 30 and container 3, influences the dependency on the number of actuations, in particular such that the gradient of the curves C2 and C3 is less than the gradient of curve C1 with lower total volume/air buffer. Therefore, a higher total air volume/air buffer may be advantageous to achieve a more uniform operation.

Further, the above comparison shows that the lower total air volume leads to a higher air pressure level which might lead to undesired fluid leakage. Thus, the control of the air pressure—preferably by means of valve 40 or 43—might be advantageous in particular in this case. However, the effect of the optional valve 40/43 has not been considered in curves C1 to C3.

The comparison of curves C2 and C3 shows that the influence of the volume of the withdrawn dose of the fluid 2 is relatively small in comparison to the influence of the total air volume, but with higher volume of each dose the curve C3 declines faster than the curve C2 with smaller volume of each dose.

Individual features, aspects and/or principles of the embodiment described may also be combined with one another as desired and may be used particularly in the shown nebulizer 1, but also in similar or different nebulizers.

Unlike freestanding equipment or the like, the proposed nebulizer 1 is preferably designed to be portable and in particular is a mobile hand operated device.

The proposed solution may, however, be used not only in the nebulizers 1 specifically described here but also in other nebulizers or inhalers or in other devices for the delivery of fluid formulations.

Preferably, the fluid 2 is, as already mentioned, a pharmaceutical formulation and in particular contains water and/or ethanol as a carrier liquid. Preferably, the expression fluid is to be broadly understood to encompass liquids, solutions, suspensions, suslutions, liquefied formulations, emulsions and the like (but not including gas-form substances or substances with a gas as a carrier).

Preferably, the fluid 2 has low vapor pressure and/or high boiling point, in particular higher than 80° C. or 90° C.

Preferably, the fluid 2 is propellant-free.

Preferred ingredients and/or formulations of the preferably medicinal fluid 2 are listed in particular in WO 2009/115200 A1, preferably on pages 25 to 40, or in EP 2 614 848 A1, paragraphs 0040 to 0087, which are incorporated herewith by reference. In particular, these may be aqueous or non-aqueous solutions, mixtures, formulations containing ethanol or free from any solvent, or the like.

Preferably the fluid 2 is a suspension with particles comprising an active ingredient such as a beta adrenergic agonists or a glucocorticosteroid.

Glucocorticosteroids that may be employed in fluid 2 to be used in systems according to the present invention include, but are not limited to, 21-acetoxypregnenolone, alclometasone, algestone, amcinonide, beclomethasone, betamethasone, budesonide, chloroprednisone, ciclesonide, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluiticasone/fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone/mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, (11b, 16a)-16,17-[butylidenebisbis(oxy)]-11, 21-dihydroxy-16-methylpregna-1,4-diene-3,20-dione 21-[(4'-nitrooxymethyl)benzoate] and derivatives, analogues, enantiomer forms, stereoisomers, anhydrides, acid addition salts, base salts, solvates, and combinations thereof.

Preferably, the fluid 2 comprises at least one dispersion enhancer selected from the group consisting of polysorbate 20, polysorbate 40, polysorbate 60, polysorbate 80, lecithin, polyethylene glycol, polyvinylpyrrolidone, poloxamer and sodiumlaurylsulfate.

Alternative Embodiments

Further aspects of the present invention are:

1. System comprising a nebulizer (1) for nebulizing a fluid (2) and a container (3) containing multiple doses of the fluid (2), wherein the nebulizer (1) comprises a fluid pump (5) for withdrawing a dose of the fluid (2) from the container (3) and pressurizing the respective dose for nebulization with operational pressure of 5 to 250 MPa, in particular 10 to 50 MPa, and a microstructured component forming a nozzle (12) with nozzle channels (12*d*) having a hydraulic diameter in the range of 3 to 20 microns, in particular 4 to 12 microns, most preferably 5 to 8 microns characterized in that the fluid (2) is a structured fluid and/or a non-newtonian fluid, in particular wherein the fluid (2) has a shear rate dependent or stress dependent viscosity.

2. System according to aspect 1 characterized in that the viscosity drops at higher rates of shear velocity resp. stress and/or in that the fluid (2) has a shear-thinning/pseudoplastic behavior.
3. System according to aspect 1 or 2 characterized in that the fluid (2) comprises a carrier liquid which has a viscosity of up to $1.600*10^{-3}$ Pascal seconds (1.6 centiPoise) or a viscosity not exceeding 1.6 centiPoise, in particular wherein the carrier liquid is water or ethanol or a mixture of water and ethanol.

4. System according to one of the preceding aspects characterized in that the fluid (2) is a suspension of nanoparticles.
5. System according to aspect 4 characterized in that the nanoparticles comprising an active ingredient such as a beta adrenergic agonists or a glucocorticosteroid.
6. System according to aspect 4 or 5 characterized in that the nanoparticles have a concentration of up to 10%, preferably up to 7%, and in particular more than 1% in the fluid (2).
7. System according to one of aspects 1 to 3 characterized in that the fluid (2) is an emulsion, in particular an "oil-in-water"-emulsion.
8. System according to one of the previous aspects characterized in that the fluid (2) is a liposomal fluid.
9. System according to aspect 8, characterized in that the fluid (2) comprises liposomes or lipid droplets or lipid particles wherein the liposomes or lipid droplets or lipid particles comprise a dissolved or embedded active ingredient.
10. System according to aspect 8 or 9, characterized in that the liposomal fluid comprises a physiological lipid, in particular a phospholipid, preferably lecithine or a mixture of lecithine and cholesterol.
11. System according to one of the preceding aspects, wherein the fluid (2) comprises less than 17% glycerin, in particular less than 10% glycerin or most preferably less than 1% or no glycerin.
12. System according to one of aspects 1 to 3 characterized in that the fluid (2) is a gel or comprises a gelling agent, in particular wherein the fluid (2) contains 8,5% or less gelling agent, preferably less than 2% gelling agent.
13. System according to one of the preceding aspects, characterized in that container (3) comprises a variable or collapsible or compressible volume (4) containing the fluid (2).
14. System according to aspect 13, characterized in that the container (3) comprises a collapsible bag as a collapsible volume (4) containing the fluid (2).
15. System according to aspect 13, characterized in that the container (3) comprises a rigid casing (20) and a fluid piston (28) moveable therein forming a space for directly receiving the fluid (2) or the variable or compressible volume (4) containing the fluid (2).
16. System according to one of aspects 13 to 15, characterized in that the system comprises a means to pressurizing the fluid (2) in the container (3) or a means to apply pressure to the variable or collapsible or compressible volume (4) containing the fluid (2), in particular wherein the means pressurizes the fluid (2) (in addition to the ambient pressure) with a pressure of 0.05 to 3 bars or can apply a pressure of 0.05 to 3 bars, preferably 0.2-1 bar or 1-2 bars, during the withdrawal of fluid (2) from the container (3).
17. System according to one of aspects 13 to 16, characterized in that during withdrawal of the fluid (2) the pressure onto the variable or collapsible or compressible volume (4) is applied in the direction of a fluid outlet of the container (3) and/or in the direction of a fluid entrance, in particular a conveying tube (9), into the nebulizer (1).
18. System according to aspect 16, characterized in that the means is formed by or comprises an air pump (30) associated to the container (3) for pressurizing the fluid (2) in the container (3) to help withdrawing the fluid (2) in doses from the container (3).
19. System according to aspect 18, characterized in that during use of the nebulizer (1), the air pump (30) and the fluid pump (5) pressurize alternately, in particular the air pump (30) pressurizes air when tensioning or loading the nebulizer (1) and the fluid pump (5) pressurizes a dose of fluid (2) when dispensing or nebulizing the dose of fluid (2).
20 System according to aspect 18 or 19, characterized in that the air pump (30) is actuated by a relative movement of the container (3) within a housing (1*b*) of the nebulizer (1), in particular wherein the container (3) is moveable preferably stroke-like in the nebulizer (1) when withdrawing a dose of fluid (2) and/or when pressurizing or dispensing a dose of the fluid (2).
21. System according to any one of aspects 18 to 20, characterized in that the air pump (30) comprises or forms a piston/cylinder arrangement for pumping air to help withdrawing the fluid (2) in doses from the container (3).
22. System according to any one of aspects 18 to 22, characterized in that the container (3) drives or forms a pump piston (31) of the air pump (30), preferably cooperating with or moveable in a preferably detachable housing part (18) or an associated cylinder (32) or insert (33)
23. System according to one of aspects 18 to 23, characterized in that the nebulizer (1) or air pump (30) comprises an inlet valve (44) preventing any underpressure in the air pump (30) or its pump chamber (39).
24. System according to one of the previous aspects, characterized in that the nebulizer (1) operates purely mechanically.
25. System according to one of the previous aspects, characterized in that the nebulizer (1) is a hand-held device and/or a portable device.
26. System according to one of previous aspects, characterized in that the nebulizer (1) is an inhaler.
27. System according to one of aspects 1-25, characterized in that the nebulizer (1) is a device for ophthalmological application of the fluid (2).
28. System according to one of the previous aspects, characterized in that the fluid (2) is fabricated/produced from at least two components and wherein the container (3) comprises at least two chambers/inner volumes each containing one of the at least two components, wherein the fluid (2) is fabricated/produced by combining/mixing the two components within the container (3).
29. Method for nebulizing a fluid (2) with a nebulizer 1, wherein the nebulizer (1) comprises a fluid pump (5) for withdrawing a dose of the fluid (2) from the container (3) and pressing the respective dose with an operational pressure of 5 to 250 MPa, in particular 10 to 50 MPa, through a nozzle (12) with at least one nozzle channel (12*d*), preferably at least two nozzle channels (12*d*), having a hydraulic diameter in the range of 3 to 20 microns, in particular 4 to 12 microns, most preferably 5 to 8 microns, characterized in that the fluid (2) is fabricated/produced from at least two components, wherein the at least two components are stored within at least two (initially) fluidically separate chambers/inner volumes in a container (3), each chamber/inner volume containing one of the at least two components, and wherein the chambers/inner volumes are fluidically connected, so that at least one of the components is at least partly transferred into the other/into one of the other chambers, so that the at least two components are mixed/combined for fabricating/producing/generating the fluid (2).

30. Method according to aspect 29, characterized in that the fluid is fabricated/generated/produced before the container (3) is fluidically connected to the nebulizer (1) for nebulizing the fluid (2).

31 System comprising a nebulizer (1) for nebulizing a fluid (2) and a container (3) containing the fluid (2), wherein the nebulizer (1) comprises a fluid pump (5) for withdrawing a dose of the fluid (2) from the container (3) and pressing the respective dose with an operational pressure of 5 to 250 MPa, in particular 10 to 50 MPa, through a nozzle (12) with at least one nozzle channel (12*d*), preferably at least two nozzle channels (12*d*), having a hydraulic diameter in the range of 3 to 20 microns, in particular 4 to 12 microns, most preferably 5 to 8 microns characterized in that the fluid (2) is a gel.

| List of reference numerals | |
|---|---|
| 1 | nebulizer |
| 1b | nebulizer housing |
| 2 | fluid |
| 3 | container |
| 4 | variable/collapsible volume |
| 5 | pressure generator/fluid pump |
| 6 | holder |
| 7 | drive spring |
| 8 | blocking element |
| 8b | button |
| 9 | conveying tube |
| 10 | non-return valve |
| 11 | pressure chamber |
| 11b | pre-filter |
| 12 | nozzle |
| 12a | plate |
| 12b | cover plate |
| 12c | inflow region |
| 12d | nozzle channels |
| 12e | nozzle openings |
| 12f | fine filter |
| 12g | inlet openings (of nozzle) |
| 13 | mouthpiece |
| 14 | aerosol |
| 15 | air supply opening |
| 16 | upper housing part |
| 17 | inner part |
| 17a | upper part of inner part |
| 17b | lower part of inner part |
| 18 | housing part (lower part) |
| 18a | aeration device |
| 18b | piercing element |
| 19 | retaining element |
| 20 | (outer) casing (of container) |
| 21 | head (of container) |
| 22 | base (of container) |
| 23 | venting hole |
| 24 | shell/inner housing |
| 25 | closure |
| 26 | seal |
| 27 | venting opening |
| 28 | fluid piston |
| 28a | recess |
| 29 | seal (of fluid piston) |
| 30 | air pump |
| 31 | pump piston |
| 32 | cylinder |
| 33 | insert |
| 33a | stop |
| 34 | port |
| 35 | seal (of port) |
| 36 | return spring |
| 37 | bearing part |

-continued

| List of reference numerals | |
|---|---|
| 38 | bearing part |
| 39 | pump chamber |
| 40 | valve |
| 41 | leakage passage |
| 42 | valve element |
| 42a | flexible portion |
| 43 | inlet/check valve |
| 44 | control valve |
| 45 | opening |
| 46 | channel |
| 47 | channel |
| 48 | outlet opening |
| 49 | modified end |
| 50 | support/throttle elements |
| 125 | indicator device |
| 126 | locking device |
| C | curve |
| X | axis |
| Y | axis |

The invention claimed is:

1. A system, comprising:

a nebulizer (1) for nebulizing a fluid (2) and a container (3) containing multiple doses of the fluid (2), wherein the nebulizer (1) comprises:

a fluid pump (5) for withdrawing a dose of the fluid (2) from the container (3) and pressurizing the respective dose for nebulization with operational pressure of one of: (i) 5 to 250 MPa, and (ii) 10 to 50 MPa, and a microstructured component forming a nozzle (12) with nozzle channels (12*d*) having a hydraulic diameter in the range of one of: (i) 3 to 20 microns, (ii) 4 to 12 microns, and (iii) 5 to 8 microns, wherein at room temperature the fluid (2) has a viscosity at rest of more than one of: (i) $1.7*10^{-3}$ Pascal seconds (1.7 centipoise), and (ii) more than 0.1 Pascal seconds (10 centipoise), and the fluid (2) has a shear-thinning behavior.

2. The system according to claim 1, wherein the fluid (2), which is a structured fluid, comprises a carrier liquid which at room temperature has a viscosity of up to $1.6*10^{-3}$ Pascal seconds (1.6 centipoise), wherein the carrier liquid is water or ethanol or a mixture of water and ethanol.

3. The system according to claim 1, wherein the fluid (2) is a suspension of nanoparticles.

4. The system according to claim 3, wherein the nanoparticles comprising an active ingredient, a beta adrenergic agonists, or a glucocorticosteroid.

5. The system according to claim 3, wherein the nanoparticles have a concentration of at least one of: up to 10%, up to 7%, and more than 1% in the fluid (2).

6. The system according to claim 1, wherein the fluid (2) is at least one of: an emulsion, and an "oil-in-water" emulsion.

7. The system according to claim 1, wherein the fluid (2) is a liposomal fluid.

8. The system according to claim 7, wherein the fluid (2) comprises liposomes or lipid droplets or lipid particles wherein the liposomes or lipid droplets or lipid particles comprise a dissolved or embedded active ingredient.

9. The system according to claim 7, wherein the liposomal fluid comprises at least one of: a physiological lipid, a phospholipid, lecithine, or a mixture of lecithine and cholesterol.

10. The system according to claim 1, wherein the fluid (2) comprises at least one of: less than 17% glycerin, less than 10% glycerin, less than 1% glycerin, or no glycerin.

11. The system according to claim 1, wherein the fluid (2) at least one of: is a gel, comprises a gelling agent, contains 8.5% or less of a gelling agent, and contains less than 2% of a gelling agent.

12. The system according to claim 1, wherein the container (3) comprises a variable or collapsible or compressible volume (4) containing the fluid (2).

13. The system according to claim 12, wherein the container (3) comprises a collapsible bag as a collapsible volume (4) containing the fluid (2).

14. The system according to claim 12, wherein the container (3) comprises a rigid casing (20) and a fluid piston (28) moveable therein forming a space for directly receiving the fluid (2) or the variable or compressible volume (4) containing the fluid (2).

15. The system according to claim 12, wherein the system comprises a pressurizing mechanism to pressurize the fluid (2) in the container (3) or a mechanism to apply pressure to the variable or collapsible or compressible volume (4) containing the fluid (2), wherein the mechanism to pressurize or the mechanism to apply pressure pressurizes the fluid (2) (in addition to the ambient pressure) with at least one of: a pressure of 5000 to $3*10^5$ Pascal (0.05 to 3 bars), a pressure of 5000 to $3*10^5$ Pascal (0.05 to 3 bars), a pressure of 20000 to $10^5$ Pascal or $10^5$ to $2*10^5$ Pascal (0.2-1 bar or 1-2 bars), during the withdrawal of fluid (2) from the container (3).

16. The system according to of claim 15, wherein the mechanism to apply pressure to the variable or collapsible or compressible volume (4) is configured to apply the pressure at least one of: in the direction of a fluid outlet of the container (3) and/or in the direction of at least one of: a fluid entrance, and a conveying tube (9), into the nebulizer (1) during withdrawal of the fluid (2).

17. The system according to claim 15, wherein the mechanism to pressurize or the mechanism to apply pressure is formed by or comprises an air pump (30) associated to the container (3) for pressurizing the fluid (2) in the container (3) to help withdrawing the fluid (2) in doses from the container (3).

18. The system according to claim 17, wherein during use of the nebulizer (1), the air pump (30) and the fluid pump (5) pressurize alternately, in particular the air pump (30) pressurizes air when tensioning or loading the nebulizer (1) and the fluid pump (5) pressurizes a dose of fluid (2) when dispensing or nebulizing the dose of fluid (2).

19. The system according to claim 17, wherein at least one of: the air pump (30) is actuated by a relative movement of the container (3) within a housing (1*b*) of the nebulizer (1), and the container (3) is moveable stroke-like in the nebulizer (1) when withdrawing a dose of fluid (2) and/or when pressurizing or dispensing a dose of the fluid (2).

20. The system according to claim 17, wherein the air pump (30) comprises or forms a piston/cylinder arrangement for pumping air to help withdrawing the fluid (2) in doses from the container (3).

21. The system according to claim 17, wherein at least one of: the container (3) drives or forms a pump piston (31) of the air pump (30), the container (3) cooperates with or is moveable in a detachable housing part (18), an associated cylinder (32), or insert (33).

22. The system according to claim 17, wherein the nebulizer (1) or air pump (30) comprises an inlet valve (44) preventing any underpressure in the air pump (30) or its pump chamber (39).

23. The system according to claim 1, wherein the nebulizer (1) operates purely mechanically.

24. The system according to claim 1, wherein the nebulizer (1) is a hand-held device and/or a portable device.

25. The system according to claim 1, wherein the nebulizer (1) is an inhaler.

26. The system according to claim 1, wherein the nebulizer (1) is a device for ophthalmological application of the fluid (2).

27. The system according to claim 1, wherein the fluid (2) is fabricated/produced from at least two components and wherein the container (3) comprises at least two chambers/inner volumes each containing one of the at least two components, wherein the fluid (2) is fabricated/produced by combining/mixing the two components within the container (3).

28. The system according to claim 27, wherein the at least two components are stored within the at least two chambers and/or inner volumes in the container (3), each chamber and/or inner volume containing one of the at least two components, and the at least two chambers and/or inner volumes being initially fluidically separate, and wherein the at least two chambers and/or inner volumes are fluidically connectable, so that at least one of the components is at least partly transferred into the other and/or into one of the other chambers, so that the at least two components are mixed and/or combined for fabricating and/or producing and/or generating the fluid (2).

29. The system according to claim 28, wherein the fluid may be fabricated and/or generated and/or produced before the container (3) is fluidically connected to the nebulizer (1) for nebulizing the fluid (2).

30. The system according to claim 28, wherein the fluid (2) is a liposomal fluid.

31. The system according to claim 30, wherein the liposomal fluid is from at least a first component which comprises lecithin or dipalmitoylphosphatidylcholin (DPPC) and a second component comprising a carrier liquid, in particular an aqueous solution.

32. The system according to claim 30, wherein the liposomal fluid is at least one of: (i) from at least a first component which is solid during storage, (ii) in a form of a powder and/or, (iii) freeze-dried or lyophilized particles, and a second component which is a liquid.

* * * * *